United States Patent
Dejima et al.

(10) Patent No.: US 10,918,264 B2
(45) Date of Patent: Feb. 16, 2021

(54) SURGERY SYSTEM

(71) Applicant: FUJIFILM Corporation, Tokyo (JP)

(72) Inventors: Takumi Dejima, Kanagawa (JP); Toshiharu Kuwae, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 343 days.

(21) Appl. No.: 16/012,775

(22) Filed: Jun. 20, 2018

(65) Prior Publication Data
US 2018/0296073 A1   Oct. 18, 2018

Related U.S. Application Data

(63) Continuation of application No. PCT/JP2016/089150, filed on Dec. 28, 2016.
(Continued)

(51) Int. Cl.
*A61B 1/00* (2006.01)
*A61B 17/34* (2006.01)
(Continued)

(52) U.S. Cl.
CPC ...... *A61B 1/00135* (2013.01); *A61B 1/00128* (2013.01); *A61B 1/00133* (2013.01);
(Continued)

(58) Field of Classification Search
None
See application file for complete search history.

(56) References Cited

U.S. PATENT DOCUMENTS 5,307,804 A    5/1994   Bonnet
2012/0283663 A1*  11/2012  Delegge ............ A61M 25/0111
                                                                604/264
(Continued)

FOREIGN PATENT DOCUMENTS

JP    H09248276    9/1997
JP    2007037783   2/2007
(Continued)

OTHER PUBLICATIONS

"Search Report of Europe Counterpart Application", dated Nov. 20, 2018, p. 1-p. 6.
(Continued)

*Primary Examiner* — Timothy J Neal
(74) *Attorney, Agent, or Firm* — JCIPRNET

(57) ABSTRACT

A surgery system includes an overtube that has a distal end, a proximal end, and a longitudinal axis and holds a treatment tool and an endoscope so as to be movable forward and backward in a direction of the longitudinal axis. The overtube has an endoscope holding part that has an endoscope holding surface for holding the endoscope and allowing circumferential rotation of the endoscope about a central axis of the endoscope, and a treatment tool holding part that has a treatment tool holding surface for holding the treatment tool. The surgery system further includes an endoscope that is inserted into the overtube and has a held surface held by the endoscope holding surface. The endoscope has an orientation maintaining part that maintains the circumferential orientation of the endoscope even in a case where the overtube rotates around the longitudinal axis.

18 Claims, 20 Drawing Sheets

Related U.S. Application Data

(60) Provisional application No. 62/275,792, filed on Jan. 7, 2016.

(51) Int. Cl.
*A61B 1/05* (2006.01)
*A61B 1/06* (2006.01)
*A61B 17/29* (2006.01)

(52) U.S. Cl.
CPC .............. *A61B 1/05* (2013.01); *A61B 1/0661* (2013.01); *A61B 17/2909* (2013.01); *A61B 17/3421* (2013.01); *A61B 2017/3445* (2013.01)

(56) References Cited

U.S. PATENT DOCUMENTS

| | | |
|---|---|---|
| 2015/0080650 A1 | 3/2015 | Dejima et al. |
| 2016/0015255 A1 | 1/2016 | Dejima |
| 2017/0007100 A1 | 1/2017 | Dejima |
| 2017/0007101 A1 | 1/2017 | Dejima |
| 2017/0007294 A1 | 1/2017 | Iwasaka et al. |

FOREIGN PATENT DOCUMENTS

| | | |
|---|---|---|
| WO | 2013176167 | 11/2013 |
| WO | 2014157477 | 10/2014 |
| WO | 2015122474 | 8/2015 |
| WO | 2015147157 | 10/2015 |
| WO | 2015147158 | 10/2015 |
| WO | 2015147159 | 10/2015 |

OTHER PUBLICATIONS

"Office Action of Europe Counterpart Application", dated Mar. 16, 2020, p. 1-p. 4.

"International Search Report (Form PCT/ISA/210) of PCT/JP2016/089150", dated Mar. 7, 2017, with English translation thereof, pp. 1-6.

"Written Opinion (Form PCT/ISA/237)", dated Mar. 7, 2017, with English translation thereof, pp. 1-22.

"Office Action of Europe Counterpart Application", dated Sep. 16, 2020, p. 1-p. 5.

* cited by examiner

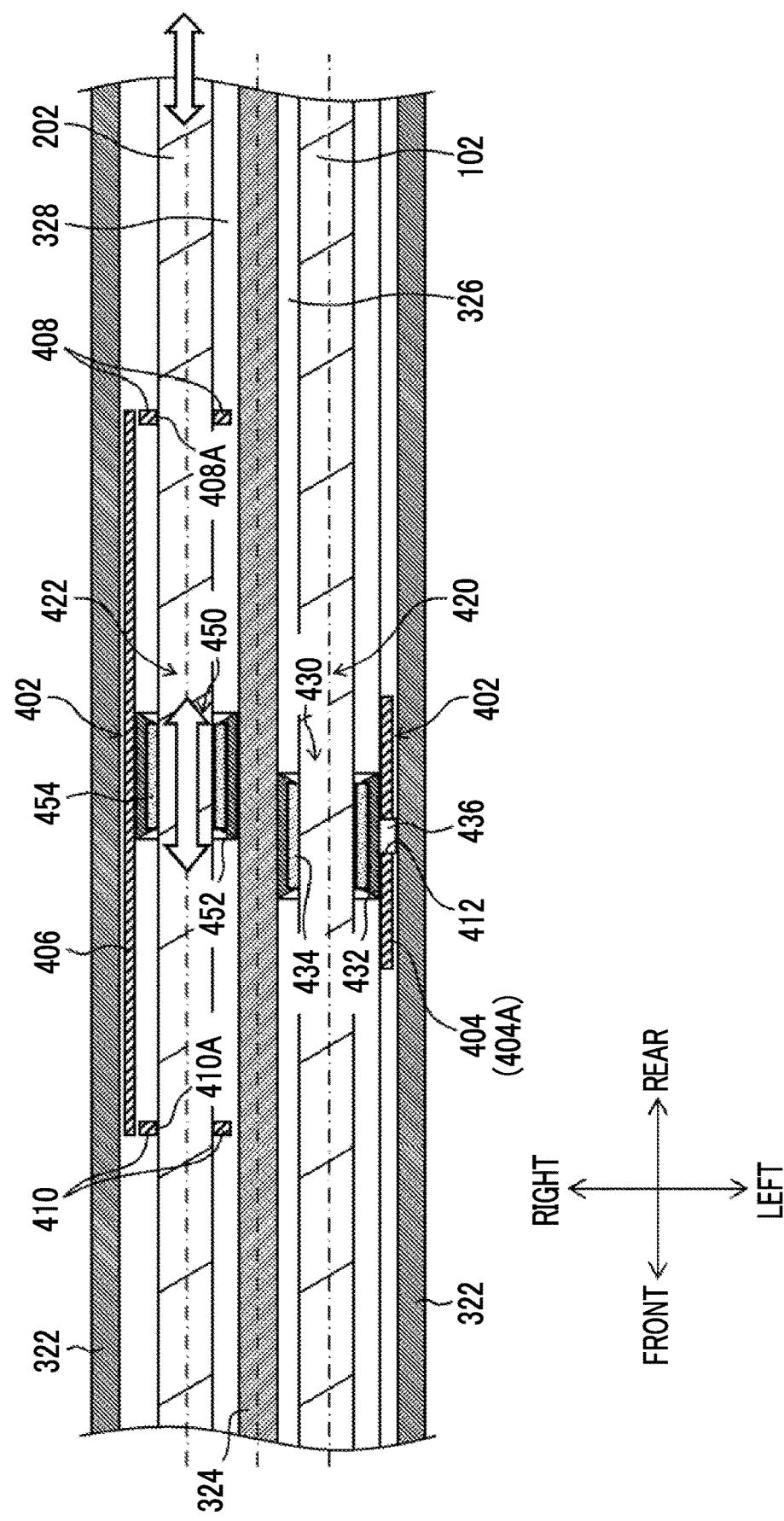

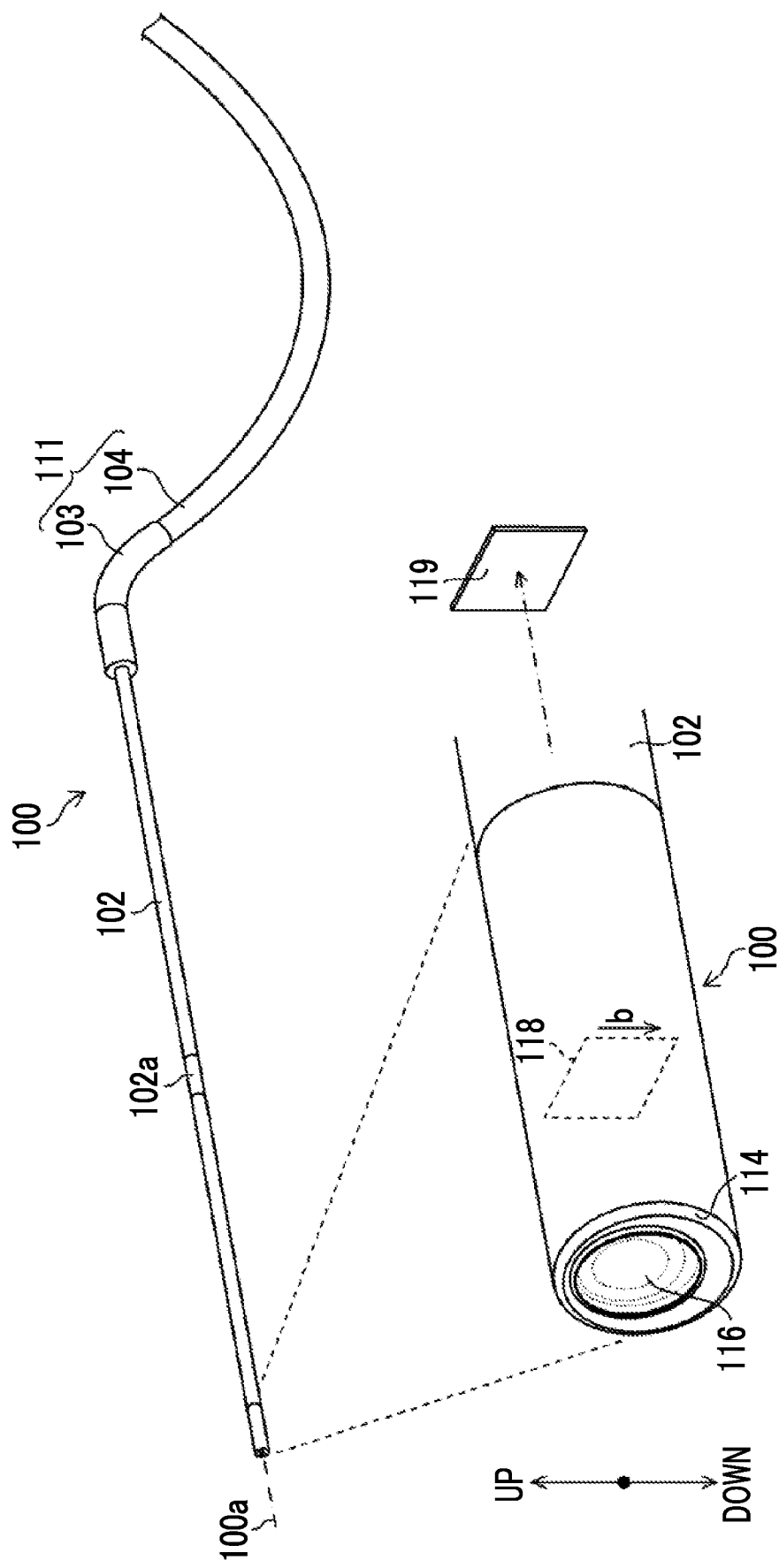

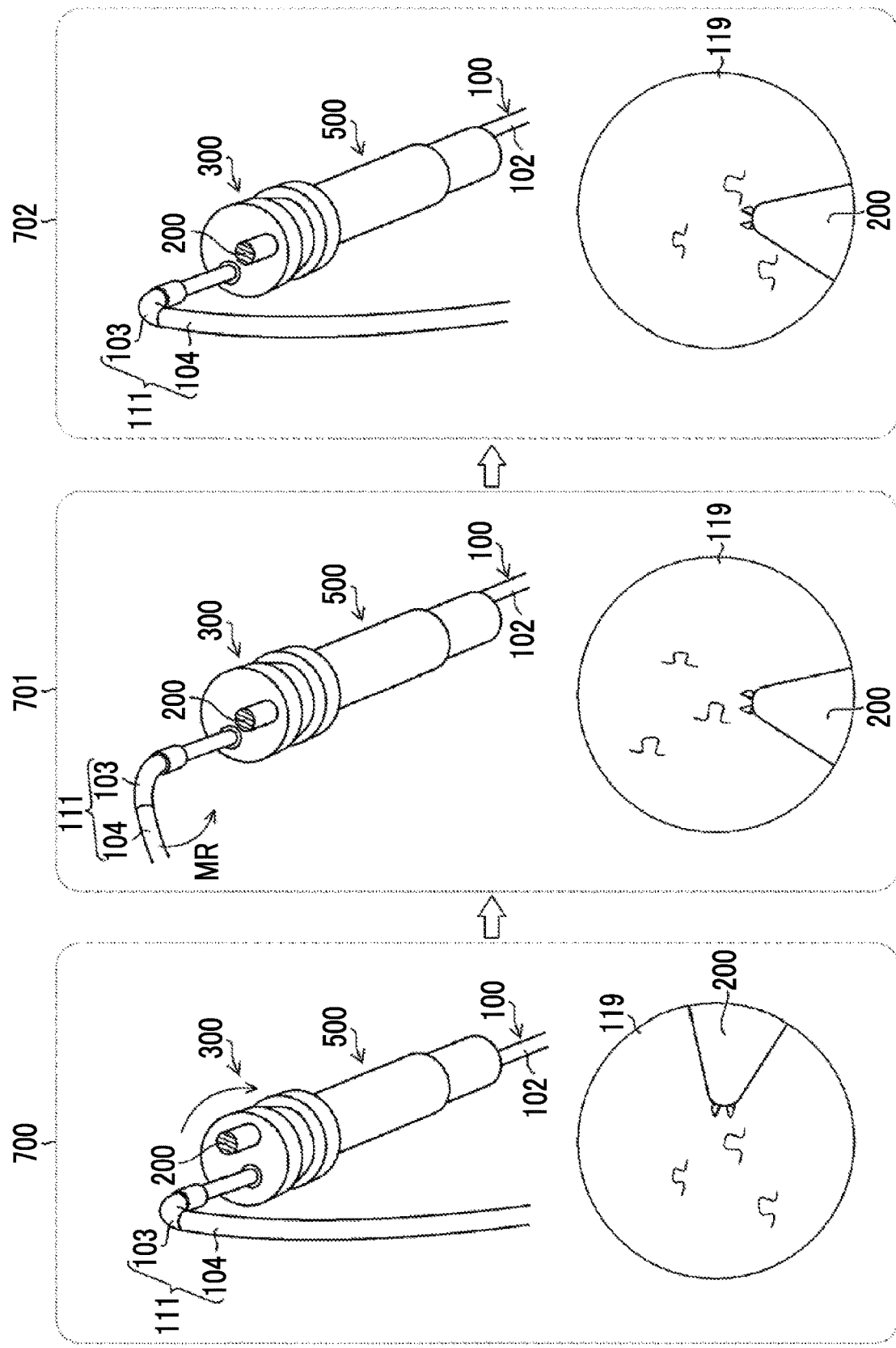

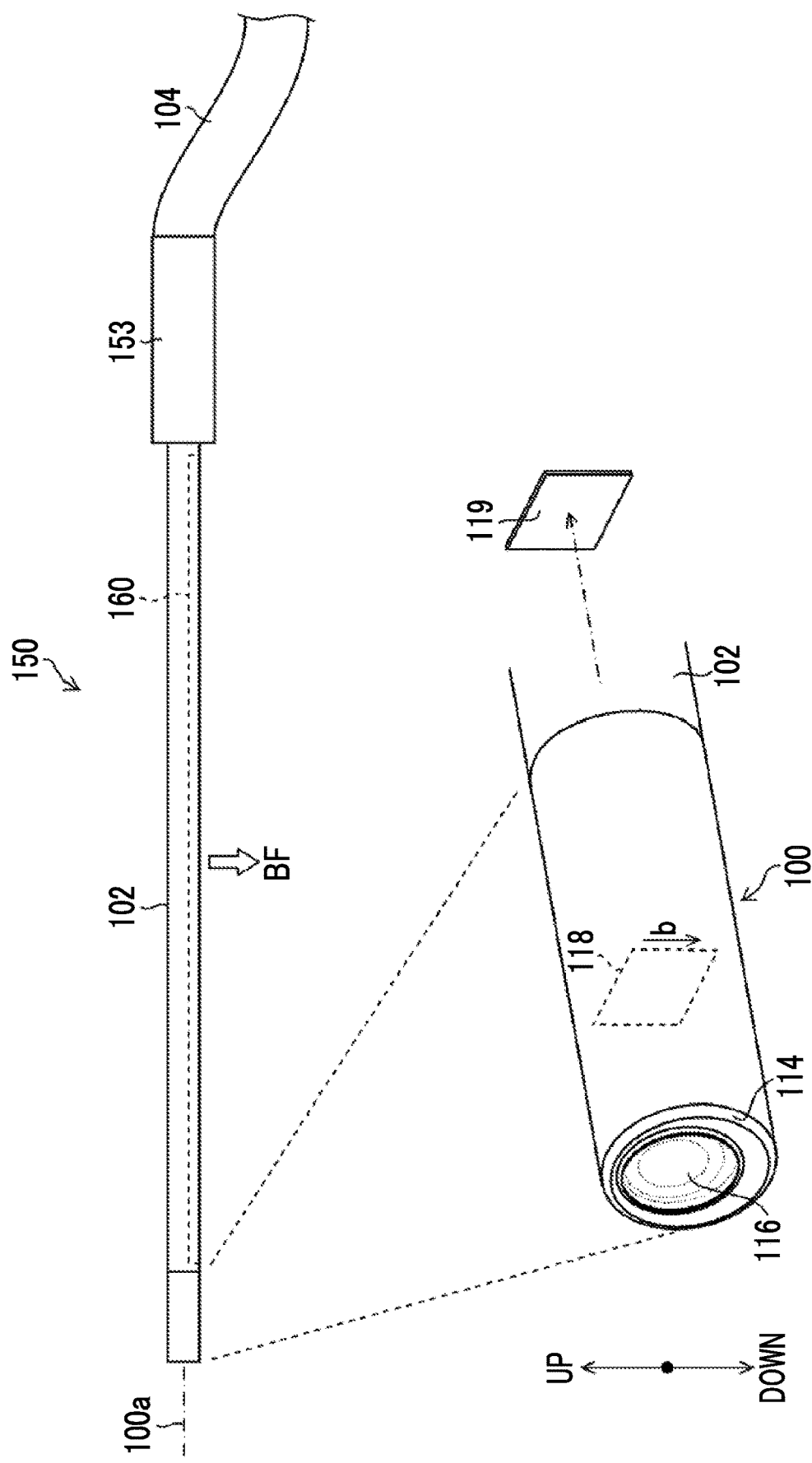

SURGERY SYSTEM

CROSS-REFERENCE TO RELATED APPLICATIONS

The present application is a Continuation of PCT International Application No. PCT/JP2016/089150 filed on Dec. 28, 2016 claiming priority under 35 U.S.C. § 119(a) to U.S. Provisional Application No. 62/275,792 filed on Jan. 7, 2016. Each of the above applications is hereby expressly incorporated by reference, in their entirety, into the present application.

BACKGROUND OF THE INVENTION

1. Field of the Invention

The present invention relates to an endoscope, and a surgery system having an overtube that holds an endoscope and a treatment tool so as to be movable forward and backward.

2. Description of the Related Art

In recent years, since the invasion to a patient is small compared to surgery in which a laparotomy, a thoracotomy, or the like is performed, endoscopic surgery using endoscopes (rigid endoscopes), such as a laparoscope, has been widely performed. In the endoscopic surgery, a plurality of holes are made in a patient's body wall, an endoscope is inserted into a body cavity from one hole among the plurality of holes, and a treatment tool is inserted into the body cavity from another hole. Then, treatment of living body tissue is performed with the treatment tool while displaying endoscopic images obtained by the endoscope on a monitor to observe the living body tissue within the body cavity.

In such endoscopic surgery, an insertion part of the endoscope and an insertion part of the treatment tool can be inserted into the body cavity by using an overtube (also referred to as a trocar) having a plurality of insertion passages through which the insertion part of the endoscope and the insertion part of the treatment tool are inserted, respectively (refer to WO2013/176167A). By using the overtube described this WO2013/176167A, the number of holes to be made in the patient's body wall can be reduced, and the invasion to the patient can be suppressed.

Additionally, the overtube described in WO2013/176167A is inserted through an outer sheath (also referred to as a sheathing tube) fixed to the body wall in a state where the overtube is inserted into the body cavity and is held by this outer sheath so as to be rotatable around a longitudinal axis. Accordingly, the protruding position of the treatment tool on an endoscopic image displayed on a monitor can be changed by rotating the overtube relative to the outer sheath.

SUMMARY OF THE INVENTION

Meanwhile, in a case where the overtube is rotated relative to the outer sheath in order to change the protruding position of the treatment tool on the endoscopic image, the entire overtube through which the endoscope and the treatment tool are inserted rotates. For this reason, in a case where the endoscope rotates around the longitudinal axis of the overtube as a center together with the rotation of the overtube, the top and bottom of the endoscopic image displayed on the monitor will change. Thus, a problem occurs in that the endoscopic image becomes difficult to see.

The invention has been made in view of such circumstances, and an object thereof is to provide a surgery system that can suppress a change in perspective of an endoscopic image on a monitor even in a case where an overtube has rotated.

A surgery system for achieving the object of the invention comprises an overtube that has a distal end, a proximal end, and a longitudinal axis and holds a treatment tool and an endoscope so as to be movable forward and backward in the direction of the longitudinal axis. The overtube has an endoscope holding part that has an endoscope holding surface for holding the endoscope and allowing circumferential rotation of the endoscope about a central axis of the endoscope, and a treatment tool holding part that has a treatment tool holding surface for holding the treatment tool. The surgery system further comprises an endoscope that is inserted into the overtube and has a held surface held by the endoscope holding surface. The endoscope has an orientation maintaining part that maintains the circumferential orientation of the endoscope even in a case where the overtube rotates around the longitudinal axis.

According to this surgery system, the change in perspective of the endoscopic image displayed on the monitor can be suppressed even in a case where the overtube rotates around the longitudinal axis.

In the surgery system related to another aspect of the invention, the orientation maintaining part has a rotational moment generation part that generates a rotational moment around the central axis of the endoscope in a case where the overtube has rotated around the longitudinal axis, and maintains the orientation of the endoscope using the rotational moment generated in the rotational moment generation part. Accordingly, the change in perspective of the endoscopic image displayed on the monitor can be suppressed even in a case where the overtube rotates around the longitudinal axis.

In the surgery system related to a further aspect of the invention, the rotational moment generation part has a biasing member that biases a circumferential position of the endoscope to a fixed position. The rotational moment that maintains the circumferential orientation of the endoscope in a case where the overtube has rotated around the longitudinal axis can be generated around the central axis of the endoscope by the biasing of the biasing member.

In the surgery system related to a still further aspect of the invention, the biasing member has a gravity center position at a position eccentric from the central axis of the endoscope. Accordingly, the rotational moment can be generated around the central axis of the endoscope in a case where the overtube has rotated around the longitudinal axis.

In the surgery system related to a still further aspect of the invention, the endoscope has a rigid insertion part inserted into the overtube, a flexible cord part provided on a proximal end side of the insertion part, a connecting part connecting the insertion part and the cord part to each other, and at least a portion of the connecting part is provided obliquely with respect to a central axis of the insertion part of the endoscope, and the rotational moment generation part, the connecting part, and the cord part as the biasing member, and generates a rotational moment around the central axis of the endoscope with the connecting part and the cord part in a case where the overtube has rotated around the longitudinal axis. The rotational moment that maintains the circumferential orientation of the endoscope can be generated around the central axis of the endoscope simply by partially changing the configuration of an existing endoscope.

In the surgery system related to a still further aspect of the invention, the biasing member has a weight member that is provided on the endoscope, and biases the circumferential position of the endoscope to a fixed position using the weight of the weight member. The rotational moment that maintains the circumferential orientation of the endoscope can be generated around the central axis of the endoscope simply by providing the weight member on an existing endoscope.

In the surgery system related to a still further aspect of the invention, the endoscope has a gravity center position at a position eccentric from the central axis of the endoscope, and the rotational moment generation part generates a rotational moment, resulting from gravity, about the central axis at the gravity center position of the endoscope. The circumferential orientation of the endoscope can be maintained using the rotational moment resulting from gravity in a case where the overtube has rotated around the longitudinal axis.

In the surgery system related to a still further aspect of the invention, the overtube has a movable body that is movable in a direction of the longitudinal axis, and the endoscope holding part and the treatment tool holding part are provided at the movable body. Accordingly, the endoscope and the treatment tool can be moved in an interlocking manner in the longitudinal axis direction via the movable body.

In the surgery system related to a still further aspect of the invention, the movable body has a distal-end-side restricting part that restricts movement of the endoscope holding part on a distal end side of the movable body, and a proximal-end-side restricting part that restricts movement of the endoscope holding part on a proximal end side of the movable body, and the endoscope holding part is movable between the distal-end-side restricting part and the proximal-end-side restricting part. Accordingly, the movement of the endoscope holding part can be allowed in a range between the distal-end-side restricting part and the proximal-end-side restricting part and can be restricted within the range.

A surgery system for achieving the object of the invention comprises an overtube that has a distal end, a proximal end, and a longitudinal axis and holds a treatment tool and an endoscope so as to be movable forward and backward in a direction of the longitudinal axis. The overtube has an endoscope holding part that has an endoscope holding surface for holding the endoscope, and a treatment tool holding part that has a treatment tool holding surface for holding the treatment tool. The surgery system further comprises an endoscope that is inserted into the overtube and has a held surface held by the endoscope holding surface. The endoscope has a rotational moment generation part that generates a rotational moment around the central axis of the endoscope in a case where the overtube has rotated around the longitudinal axis. The rotational moment generated in the rotational moment generation part is greater than a friction moment, about the central axis of the endoscope, resulting from a frictional force between the endoscope holding surface and the held surface.

According to this surgery system, a greater rotational moment than the friction moment is generated even in a case where the overtube rotates around the longitudinal axis. Thus, the endoscope can be rotated such that the circumferential orientation of the endoscope is maintained using this rotational moment.

In the surgery system related to another aspect of the invention, the rotational moment generation part has a biasing member that biases a circumferential position about the central axis of the endoscope to a fixed position. The rotational moment that maintains the circumferential orientation of the endoscope in a case where the overtube has rotated around the longitudinal axis can be generated around the central axis of the endoscope by the biasing of the biasing member.

A surgery system for achieving the object of the invention comprises an overtube that has a distal end, a proximal end, and a longitudinal axis and holds a treatment tool and an endoscope so as to be movable forward and backward in a direction of the longitudinal axis. The overtube has an endoscope holding part that has an endoscope holding surface for holding the endoscope, and a treatment tool holding part that has a treatment tool holding surface for holding the treatment tool. The surgery system further comprises an endoscope that is inserted into the overtube and has a held surface held by the endoscope holding surface. The endoscope has a gravity center position at a position deviating from the central axis of the endoscope. A rotational moment, resulting from gravity, about the central axis in the gravity center position of the endoscope is greater than a friction moment, about the central axis, resulting from a frictional force between the endoscope holding surface and the held surface.

According to this surgery system, the circumferential orientation of the endoscope can be maintained using the rotational moment resulting from gravity even in a case where the overtube rotates around the longitudinal axis. Thus, the change in perspective of the endoscopic image displayed on the monitor can be suppressed.

In the surgery system related to another aspect of the invention, the overtube has a movable body that is movable in a direction of the longitudinal axis inside the overtube, and the movable body has an endoscope locking part to which the endoscope holding part is locked, and a treatment tool locking part to which the treatment tool holding part is locked. The endoscope and the treatment tool can be moved in an interlocking manner in the longitudinal axis direction.

In the surgery system related to a further aspect of the invention, the movable body has a non-sensing region where the forward and backward movement of either the endoscope or the treatment tool does not interlock with the forward and backward movement of the other and a sensing region where the forward and backward movement of either the endoscope or the treatment tool interlocks with the forward and backward movement of the other. Hence, since the endoscope does not move forward and backward with respect to the forward and backward movement operation thereof in a non-sensing region, the range of an observation site, such as a distal end site of the treatment tool or a body cavity inner site, to be displayed as the endoscopic image on the monitor does not vary, and the size of an image of the observation site can be prevented from fluctuating in accordance with minute displacement of the treatment tool. Accordingly, a sense of perspective can be suitably maintained, and a stable endoscopic image can be obtained. Additionally, since the endoscope moves forward and backward with respect to the forward and backward movement operation in the sensing region, the range of the observation site that appears in the endoscopic image to be displayed on the monitor is continuously changed so as to follow the forward and backward movement of the treatment tool. Since the size of images of observation sites other than the distal end site of the treatment tool that appears in the endoscopic image in accordance with the operation of the treatment tool, and the size of the range of the observation site changes, the operator can simply obtain a desired image.

The surgery system related to a still further aspect of the invention further comprises an outer sheath that has a distal end opening and a proximal end opening and has an insertion passage through which the overtube is inserted from the proximal end opening so as to be rotatable around the longitudinal axis. Accordingly, the protruding position of the treatment tool on the endoscopic image can be changed by rotating the overtube relative to the outer sheath.

A surgery system for achieving the object of the invention comprises an overtube that has a distal end, a proximal end, and a longitudinal axis and holds a treatment tool and an endoscope so as to be movable forward and backward in a direction of the longitudinal axis. The overtube has an endoscope holding part that has an endoscope holding surface for holding the endoscope and allowing circumferential rotation of the endoscope about a central axis of the endoscope, and a treatment tool holding part that has a treatment tool holding surface for holding the treatment tool. The surgery system further comprises an endoscope that is inserted into the overtube. The endoscope has an insertion part that has a distal end, a proximal end, and a central axis in a direction of the longitudinal axis, a cord part provided on a proximal end side of the insertion part, a connecting part that connects the insertion part and the cord part to each other, an image pick-up element provided on a distal end side of the insertion part, a held surface provided at the insertion part and held by the endoscope holding surface, a rotational moment application part that applies a rotational moment around the central axis of the insertion part to the image pick-up element. A center of gravity of the rotational moment application part is at a position eccentric from the central axis of the insertion part.

According to this surgery system, the change in perspective of the endoscopic image displayed on the monitor can be suppressed using the rotational moment applied from the rotational moment application part to the image pick-up element even in a case where the overtube rotates around the longitudinal axis.

The surgery system of the invention can prevent the change in perspective of the endoscopic image on the monitor even in a case where the overtube has rotated.

BRIEF DESCRIPTION OF THE DRAWINGS

FIG. 9 is an illustrative view for illustrating a non-sensing region of the coupling ring.

FIG. 12 is an external perspective view of the endoscope.

FIG. 15 is an illustrative view for illustrating individual circumferential orientations of the endoscope insertion part of the endoscope in a circumferential direction in a case where the overtube has rotated around the longitudinal axis, and examples of endoscopic images that are respectively displayed on a monitor in the individual circumferential orientations of the endoscope insertion part, and reference signs 700 to 702 respectively illustrate the circumferential orientations of the endoscope insertion part before and after the rotation of the overtube and the final orientation of the endoscope insertion part.

FIG. 17 is a side view of an endoscope of a further Embodiment 1 that is applicable to the surgery system.

DESCRIPTION OF THE PREFERRED EMBODIMENTS

Preferred embodiments of the invention will be described below in detail according to the accompanying drawings. In addition, any of the drawings may illustrate main parts in an exaggerated manner for description and may have dimensions different from actual dimensions.

[Overall Configuration of Surgery System]

Figure 1:
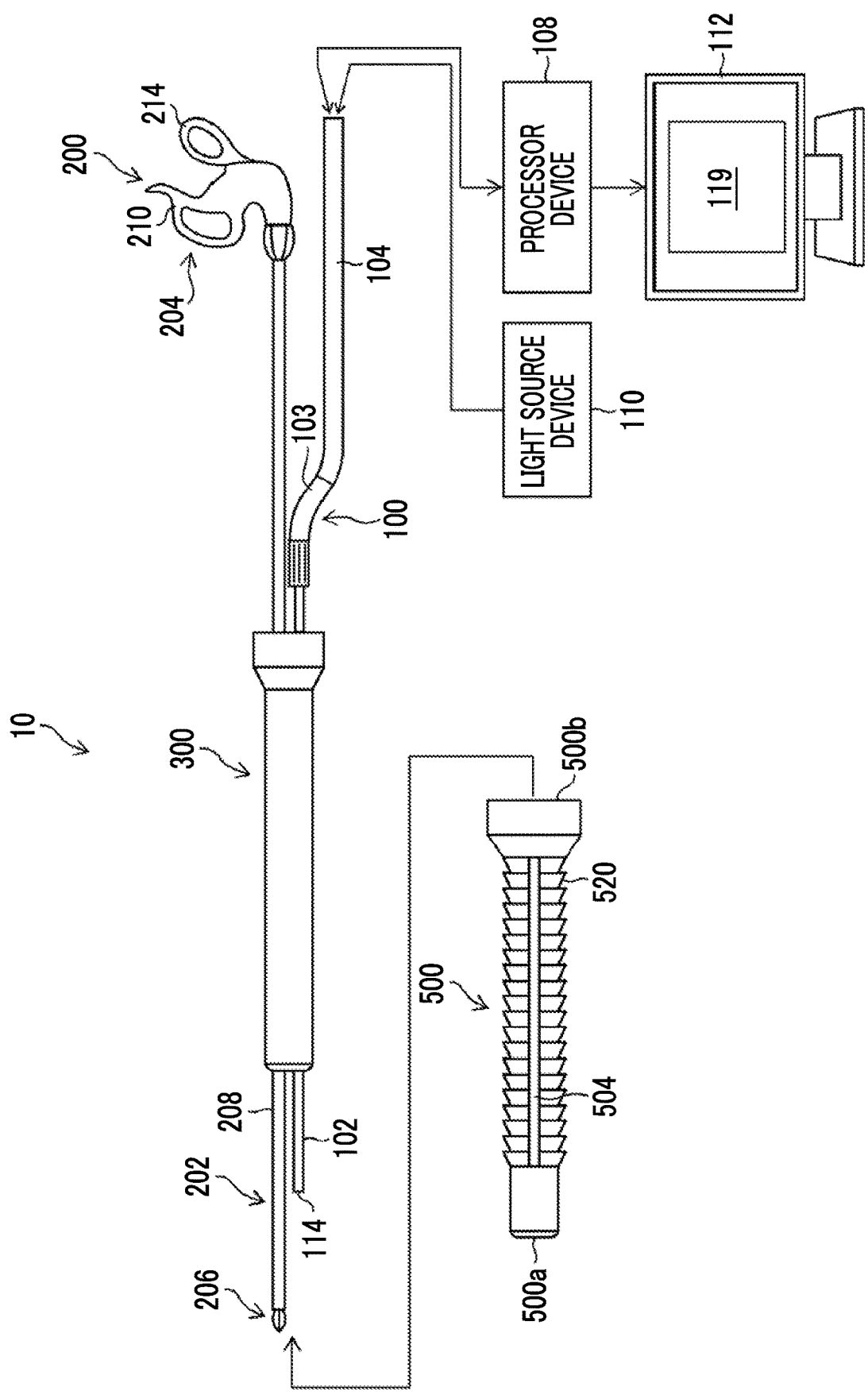
FIG. 1 is a schematic configuration view of a surgery system of the invention.

FIG. 1 is a schematic configuration view of a surgery system 10 of the invention. As illustrated in FIG. 1, the surgery system 10 includes an endoscope 100, a treatment tool 200, an overtube 300, and an outer sheath 500, and is used for observation, examination, and treatment within a body cavity of a patient.

The endoscope 100 is, for example, a rigid endoscope, such as a laparoscope, and is inserted into the body cavity to observe the inside of the body cavity. The endoscope 100 includes an elongated rigid endoscope insertion part 102 (equivalent to a rigid insertion part of the invention) to be inserted into the body cavity, a connecting part 103 continuously provided at a proximal end part of the endoscope insertion part 102, and a flexible cord part 104 connected to the endoscope insertion part 102 by the connecting part 103. A connector (not illustrated) is provided at an end of the cord part 104 opposite to a side connected to the connecting part 103, and each of a processor device 108 and a light source device 110 is detachably connected to the cord part via the connector. Additionally, a monitor 112 is connected to the processor device 108 via a cable.

A distal end part of the endoscope insertion part 102 is provided with an observation part that observes the inside of the patient's body cavity. The observation part includes an observation window 116 (refer to FIG. 12) provided on a distal end surface 114 of the endoscope insertion part 102, an illumination unit and an observation optical system (not illustrated) that are provided behind the observation window 116, and a solid-state image pick-up element 118 (refer to FIG. 12).

An exit end of a light guide (not illustrated) is disposed at the illumination unit. The light guide is inserted through the endoscope insertion part 102, the connecting part 103, and the cord part 104, extends up to the aforementioned connector, and is connected to the light source device 110. Accordingly, illumination light radiated from the light source device 110 is radiated from the illumination unit through the light guide to the front of the endoscope insertion part 102. Accordingly, the inside of the patient's body cavity is illuminated. In addition, the illumination unit may be provided behind the illumination window (not illustrated) provided on the distal end surface 114.

Subject light taken in from the observation window 116 is focused on an image pick-up surface of the solid-state image pick-up element 118 (refer to FIG. 12) by the observation optical system, and is converted into image pick-up signals by the solid-state image pick-up element 118. A signal cable (not illustrated) connected to the solid-state image pick-up element 118 is inserted through the endoscope insertion part 102, the connecting part 103, and the cord part 104, extends up to the aforementioned connector and is connected to the processor device 108. Accordingly, the processor device 108 displays an endoscopic image 119 on the monitor 112 on the basis of the image pick-up signals input from the solid-state image pick-up element 118.

The treatment tool 200 is, for example, forceps, and is inserted into the body cavity to examine or treat an affected part within the body cavity. The treatment tool 200 includes an elongated treatment tool insertion part 202 to be inserted into the body cavity, an operating part 204 that is provided on a proximal end side of the treatment tool insertion part 202 and is gripped by an operator, and a treatment part 206 that is provided at a distal end of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in an axial direction. Additionally, the operating part 204 is provided with a fixed handle 210, and a movable handle 214 that is coupled to the fixed handle 210 in a rotationally movable manner via a rotational movement pin. A proximal end part of the operating shaft is coupled to the movable handle 214.

The treatment part 206 is provided with a pair of gripping members that is openable and closable. The gripping members are coupled to a distal end part of the operating shaft via a drive mechanism (not illustrated). With the rotational movement operation of the movable handle 214 of the operating part 204, the gripping members of the treatment part 206 are opened and closed via the operating shaft and the drive mechanism.

In addition, the treatment tool 200 is not limited to the forceps, and may be, for example, other treatment tools, such as a laser probe, a suture device, an electric scalpel, a needle holder, an ultrasonic device, and an aspirator.

The overtube 300 allows the endoscope insertion part 102 and the treatment tool insertion part 202 to be inserted thereinto from the proximal end side and delivered from the distal end side. By inserting the overtube 300 into a body wall, disposing a proximal end side of the overtube outside of the body, and disposing a distal end side of the overtube within the body cavity, the endoscope insertion part 102 and the treatment tool insertion part 202 are guided into the body cavity with one overtube 300. Additionally, although the overtube 300 will be described below in detail, the overtube 300 includes an interlocking function of moving the endoscope insertion part 102 and the treatment tool insertion part 202 forward and backward in an interlocking manner. Accordingly, for example, the endoscope insertion part 102 is capable of being moved forward and backward by the forward and backward movement operation of only the treatment tool insertion part 202, and a suitable endoscopic image 119 is obtained without performing the forward and backward movement operation of the endoscope insertion part 102.

The outer sheath 500 is formed in a tubular shape, and has a distal end opening 500a and a proximal end opening 500b, and an insertion passage (not illustrated) through which the overtube 300 is rotatably inserted around the longitudinal axis toward the distal end opening 500a from the proximal end opening 500b. A number of lateral grooves 520 in the circumferential direction of the outer sheath 500 are provided at an outer peripheral part of the outer sheath 500, and longitudinal grooves 504 in a longitudinal axis direction are provided at a plurality of points in the circumferential direction of the outer sheath 500. Accordingly, in a state where the overtube 300 is inserted into the body wall together with the outer sheath 500, each lateral groove 520 restricts the forward and backward movement of the outer sheath 500 with respect to the body wall, and each longitudinal groove 504 restricts the circumferential rotation of the outer sheath 500 with respect to the body wall. Therefore, unintended rotation and forward and backward movement of the overtube 300 inserted through the outer sheath 500 with respect to the body wall are prevented. For this reason, a situation in which the position of a distal end of the endoscope insertion part 102 fluctuates and an observation visual field unintentionally fluctuates is prevented.

[Configuration of Overtube]

Figure 2:
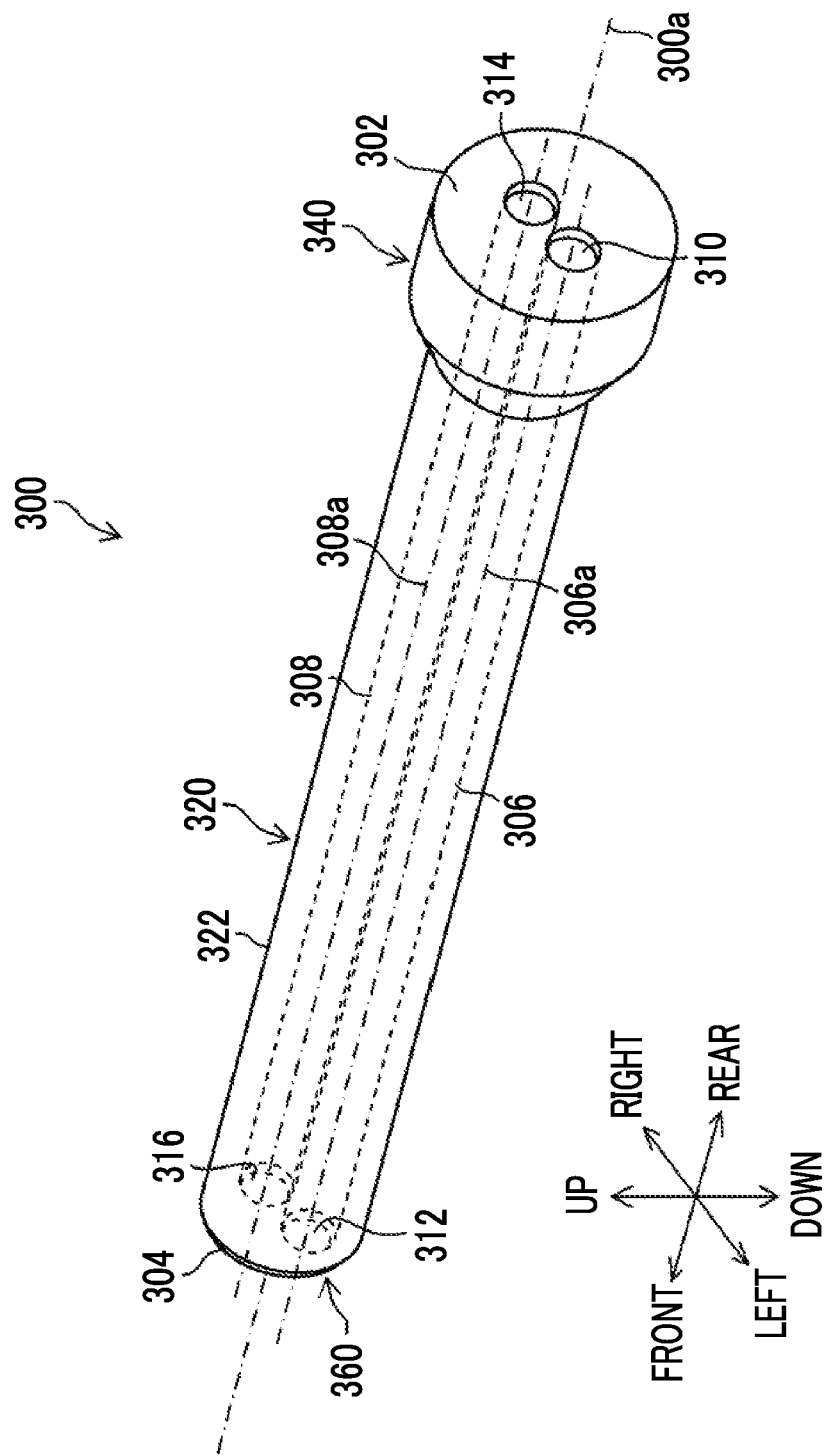
FIG. 2 is an external perspective view of an overtube.

FIG. 2 is an external perspective view of the overtube 300. As illustrated in FIG. 2, the overtube 300 has an elongated cylindrical shape as a whole, and has an endoscope insertion passage 306 through which the endoscope insertion part 102 is inserted so as to be movable forward and backward along a longitudinal axis 300a, and a treatment tool insertion passage 308 through which the treatment tool insertion part 202 is inserted so as to be movable forward and backward along the longitudinal axis 300a. The endoscope insertion passage 306 and the treatment tool insertion passage 308 are disposed parallel to each other and are disposed parallel to the longitudinal axis 300a.

Reference sign "306a" in the drawing designates an endoscope insertion axis equivalent to a central axis of the endoscope insertion passage 306. Additionally, reference sign "308a" in the drawing designates a treatment tool insertion axis equivalent to a central axis of the treatment tool insertion passage 308. In the present embodiment, although the longitudinal axis 300a, the endoscope insertion axis 306a, and the treatment tool insertion axis 308a are disposed on the same plane, these axes are not necessarily disposed on the same plane.

In addition, regarding the position and orientation of a space where the overtube 300 is disposed, terms called "forward", "backward", "left", "right", "up", and "down" are used with the orientation from a proximal end surface 302 in a direction along the longitudinal axis 300a to a distal end surface 304 defined as the forward and with the orientation from the longitudinal axis 300a to the treatment tool insertion axis 308a defined as the right. Hence, for example, the "down" is not necessarily a vertical direction perpendicular to a horizontal plane, and the "down" become non-parallel to the vertical direction in a case where the longitudinal axis 300a is not parallel to the horizontal plane (refer to FIG. 13).

The proximal end surface 302 of the overtube 300 is provided with a first proximal end opening 310 that is a proximal end opening that allows the endoscope insertion part 102 to be inserted into the endoscope insertion passage 306 therethrough, and a second proximal end opening 314 that is proximal end opening that allows the treatment tool insertion part 202 to be inserted into the treatment tool insertion passage 308 therethrough. Additionally, the distal end surface 304 of the overtube 300 is provided with a first distal end opening 312 that is a distal end opening that allows the endoscope insertion part 102 inserted into the endoscope insertion passage 306 to be delivered forward therethrough, and a second distal end opening 316 that is a distal end opening that allows the treatment tool insertion part 202 inserted into the treatment tool insertion passage 308 to be delivered forward therethrough. That is, the endoscope insertion passage 306 allows the first distal end opening 312 and the first proximal end opening 310 to communicate with each other, and the treatment tool insertion passage 308 allows the second distal end opening 316 and the second proximal end opening 314 to communicate with each other.

The overtube 300 is constituted of a long tubular overtube part 320 having a shape extending along the longitudinal axis 300a, a proximal end cap 340 that is attached to a proximal end of the long tubular overtube part 320, and a distal end cap 360 that is attached to a distal end of the long tubular overtube part 320.

The proximal end cap 340 is formed in a columnar shape of which the diameter is made larger than the external diameter of the long tubular overtube part 320 using rigid resins, metals, or the like, and a rear end surface thereof constitutes the aforementioned proximal end surface 302. Additionally, the distal end cap 360 is formed of rigid resins, metals, or the like, and a front end surface thereof constitutes the aforementioned distal end surface 304.

The long tubular overtube part 320 has a long tubular body 322 that is formed in an elongated cylindrical shape having the longitudinal axis 300a as central axis using rigid resins, metals, or the like. Additionally, the long tubular overtube part 320 has a slider 400 (refer to FIG. 3) that is an interlocking mechanism that moves the endoscope insertion passage 306 and the treatment tool insertion passage 308, and the endoscope insertion part 102 and the treatment tool insertion part 202 forward and backward in an interlocking manner in a direction of the longitudinal axis 300a (a longitudinal axis direction) within the long tubular body 322.

Figure 3A:
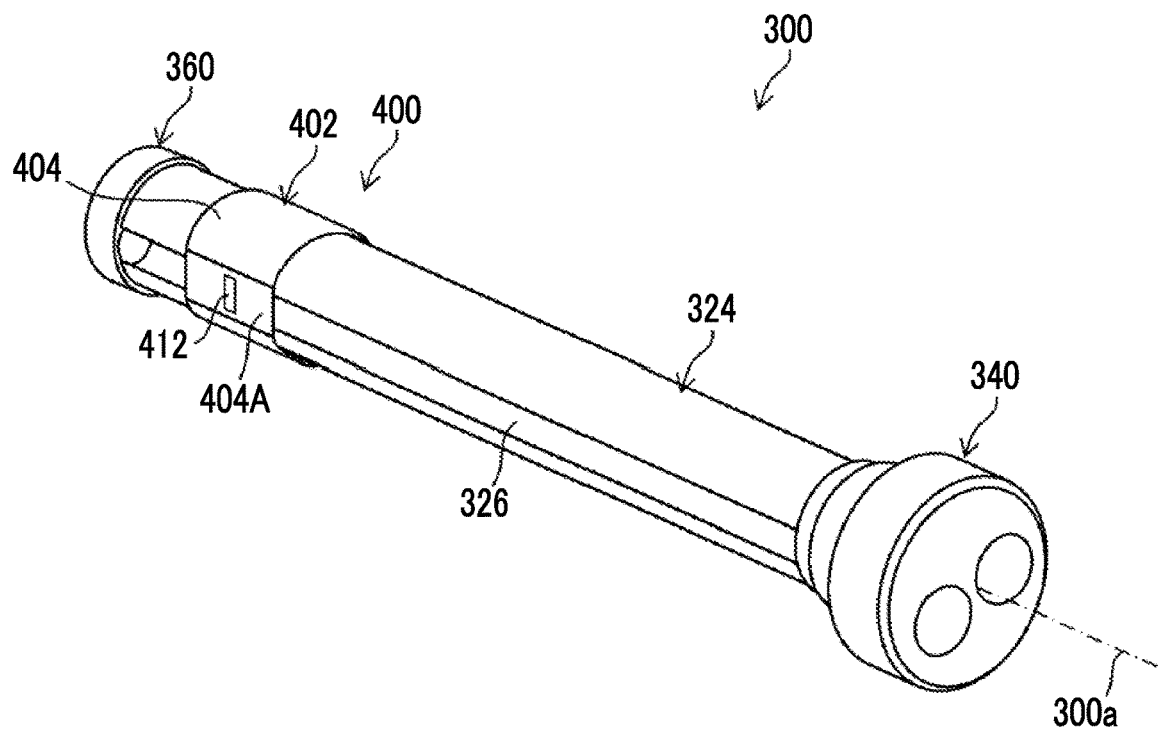
FIG. 3A is an external perspective view illustrating a long tubular overtube part with a long tubular body omitted.
Figure 3B:
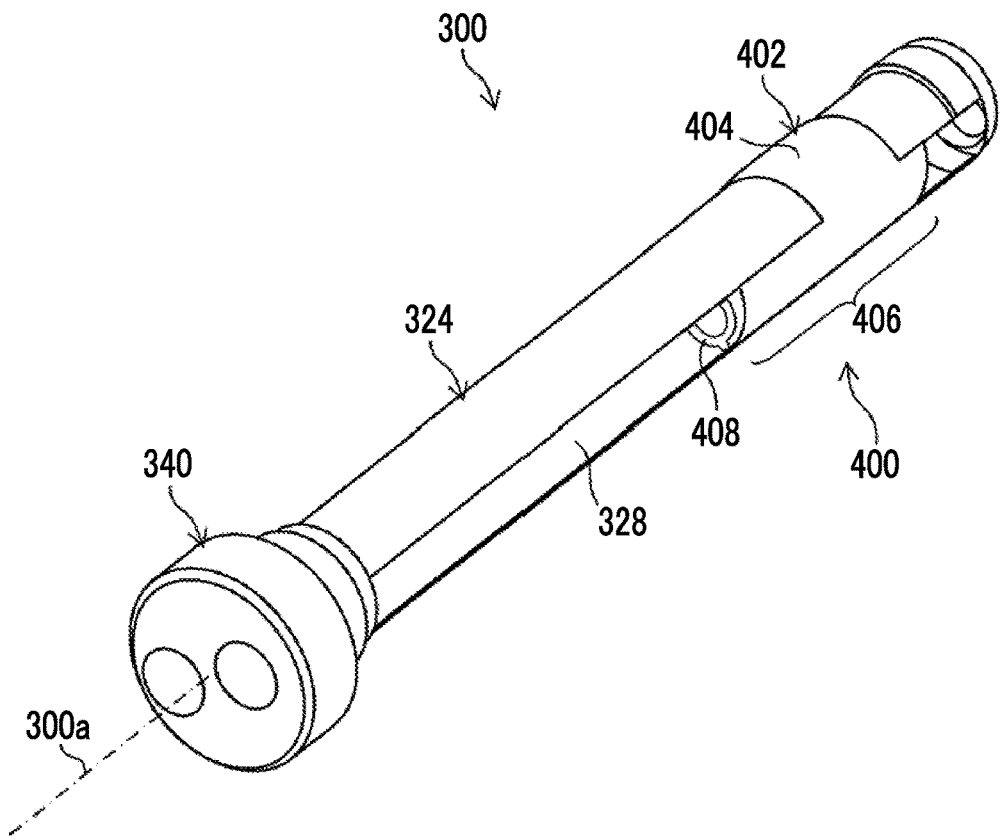
FIG. 3B is an external perspective view of the long tubular overtube part with the long tubular body omitted, as seen from a direction different from FIG. 3A.

FIGS. 3A and 3B are external perspective views illustrating the long tubular overtube part 320 with the long tubular body 322 omitted. As illustrated in FIGS. 3A and 3B, a substantially columnar partition wall member 324, which extends along the longitudinal axis 300a, and the slider 400, which is guided by the partition wall member 324 and is supported so as to be movable forward and backward in a forward-backward direction are provided within the long tubular body 322.

Figure 4:
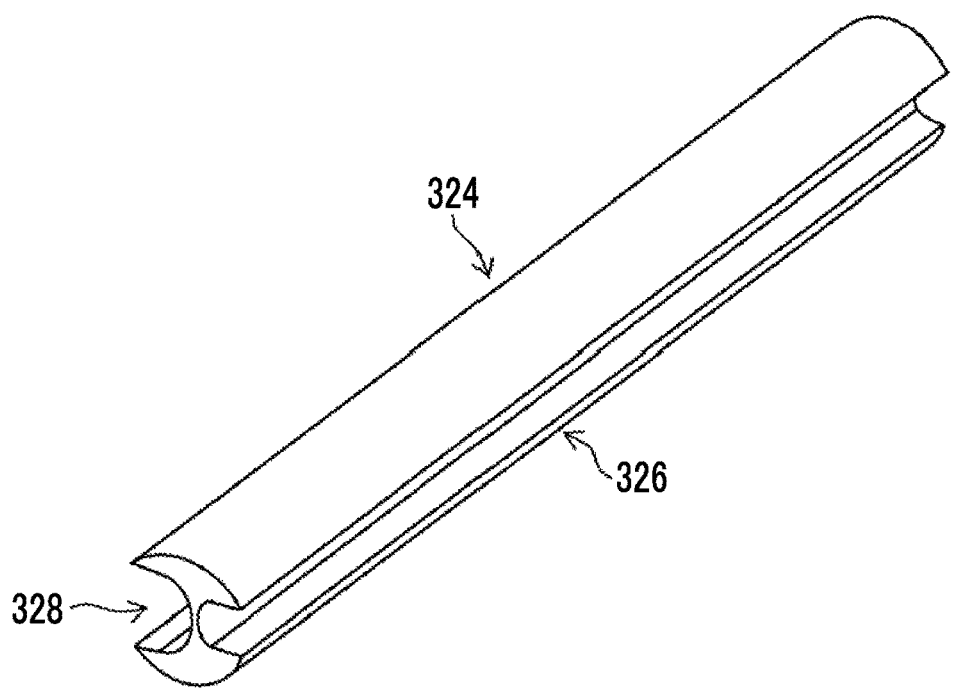
FIG. 4 is an external perspective view of a partition wall member.

FIG. 4 is an external perspective view of the partition wall member 324. As illustrated in FIG. 4, the partition wall member 324 is a solid insulator and extends from the proximal end cap 340 to the distal end cap 360 inside the long tubular body 322. An endoscope guide groove 326 and a treatment tool guide groove 328, which extend parallel to the longitudinal axis 300a from a proximal end of the partition wall member 324 to a distal end thereof, are respectively formed on a side surface of the partition wall member 324. The endoscope guide groove 326 forms a portion of the aforementioned endoscope insertion passage 306, and the treatment tool guide groove 328 forms a portion of the aforementioned treatment tool insertion passage 308. Additionally, the partition wall member 324 forms a partition wall between the endoscope insertion passage 306 and the treatment tool insertion passage 308.

By virtue of the partition wall member 324, the endoscope insertion part 102 and the treatment tool insertion part 202 inserted into the overtube 300 reliably proceed through the regions of the endoscope insertion passage 306 and the treatment tool insertion passage 308 corresponding thereto without falling out of the insertion passages, respectively. For this reason, the task of inserting the endoscope insertion part 102 and the treatment tool insertion part 202 into the overtube 300 becomes easy. Additionally, the contact between the endoscope insertion part 102 and the treatment tool insertion part 202 inside the overtube 300 is prevented, and these insertion parts are electrically insulated from each other. For that reason, even in a case where the treatment tool 200 is one using electricity, generation of electrical leakage (high-frequency electricity or the like) from the treatment tool 200 to the endoscope 100, electrical noise, or the like can be prevented, and damage or the like to the endoscope 100 can be prevented in advance.

In addition, the partition wall member 324 may be at least one that forms a partition wall between the endoscope insertion passage 306 and the treatment tool insertion passage 308, and may be not necessarily one that is formed on the basis of a columnar shape, and substantially all regions other than the endoscope insertion passage 306 and treatment tool insertion passage 308 may be hollow.

Returning to FIGS. 3A and 3B, the slider 400 is externally fitted to an outer peripheral part of the partition wall member 324 inside the long tubular body 322, and is a ring-shaped movable body that is movable forward and backward in the direction of the longitudinal axis 300a with respect to the partition wall member 324.

Figure 5:
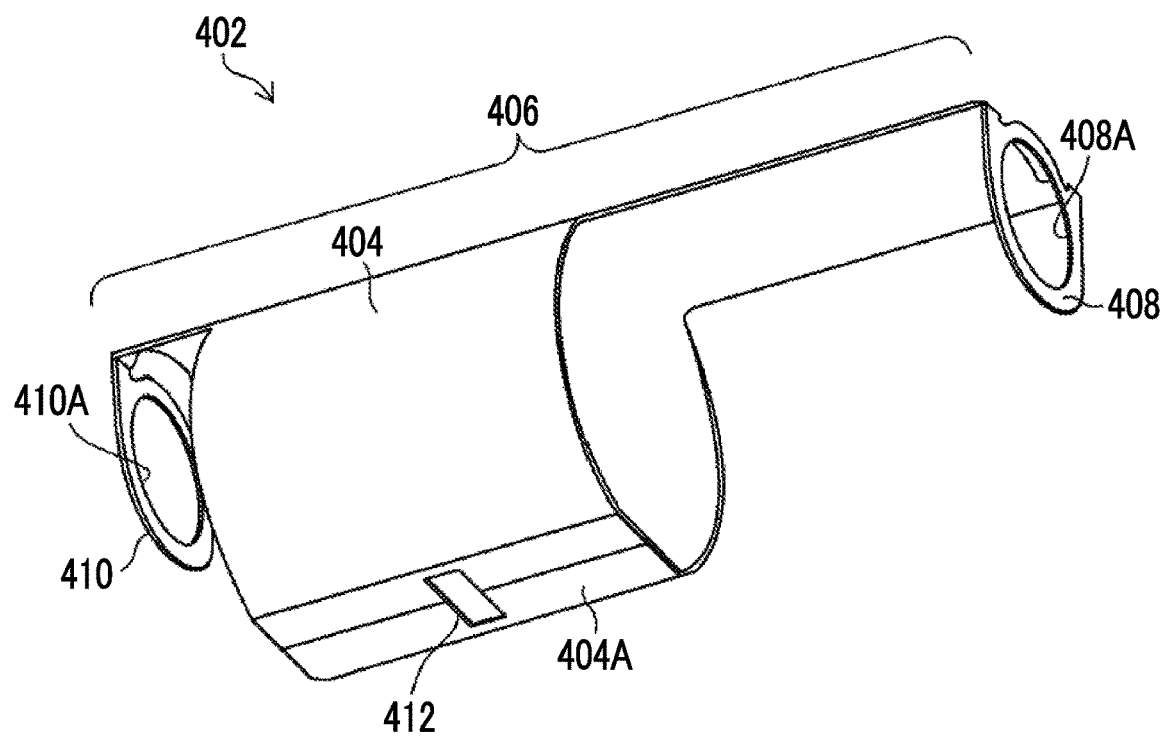
FIG. 5 is an external perspective view of a coupling ring that constitutes a portion of a slider.
Figure 6:
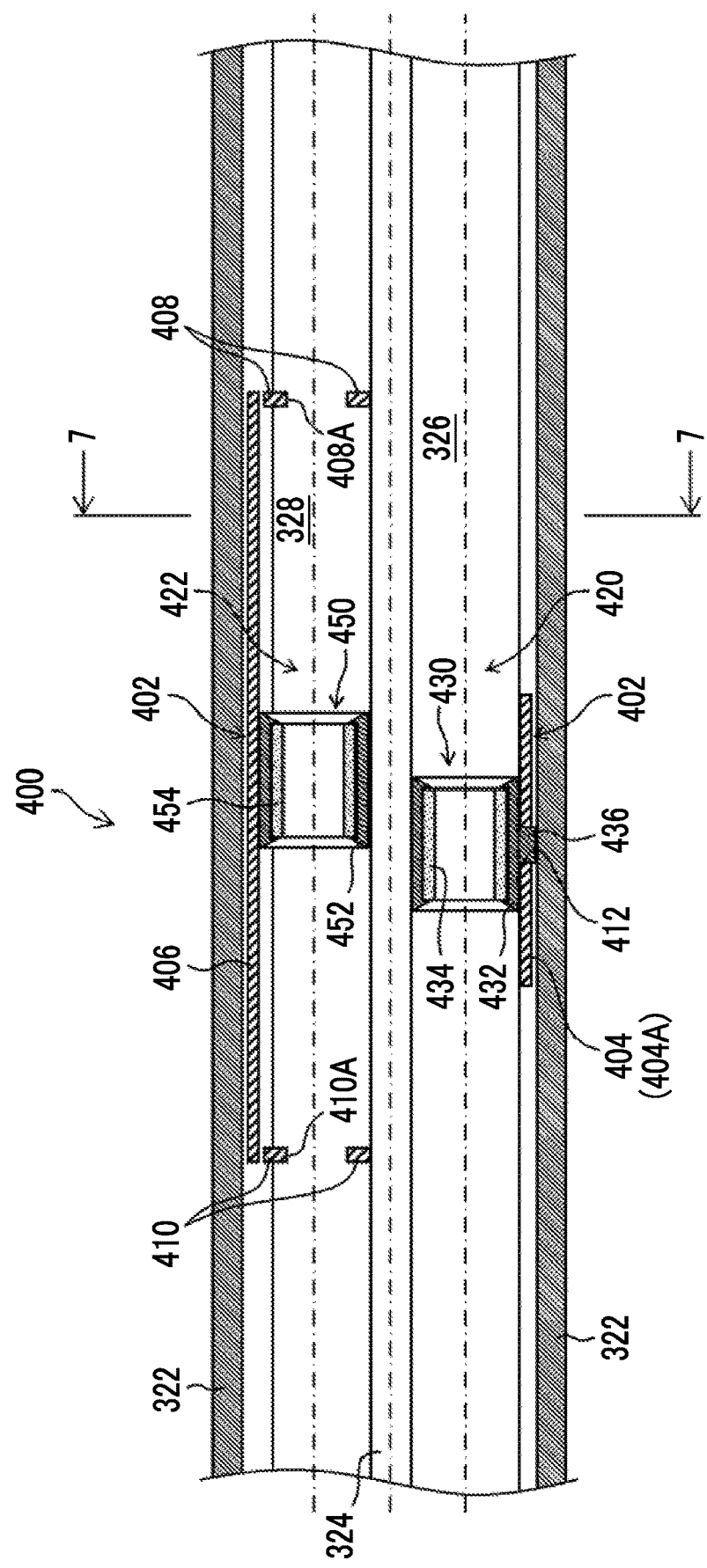
FIG. 6 is a cross sectional view of the overtube and the slider cut in a horizontal plane, including a longitudinal axis, which is orthogonal to an upward-downward direction.

FIG. 5 is an external perspective view of a coupling ring 402 that constitutes a portion of the slider 400. Additionally, FIG. 6 is a cross sectional view of the overtube 300 and the slider 400 cut in the horizontal plane, including the longitudinal axis 300a, which is orthogonal to an upward-downward direction.

As illustrated in FIGS. 3A, 3B, 5, and 6, the slider 400 has an endoscope coupling part 420 (including an endoscope holding part 434 to be described below) that is disposed inside the endoscope guide groove 326, a treatment tool coupling part 422 (including a treatment tool holding part 454 to be described below) that is disposed inside the treatment tool guide groove 328, and the coupling ring 402 that integrally interlocks the endoscope coupling part 420 and the treatment tool coupling part 422 with each other.

The coupling ring 402 has a tubular ring part 404 that surrounds an outer periphery of the partition wall member 324 in the circumferential direction, and an arm part 406. The ring part 404 is in contact with or close contact with portions other than the endoscope guide groove 326 and the treatment tool guide groove 328 in an outer peripheral surface of the partition wall member 324. Additionally, the arm part 406 extends in the forward-backward direction along the treatment tool guide groove 328 from the portion of the ring part 404 that faces the treatment tool guide groove 328.

A rear restriction end 408 and a front restriction end 410 that are disposed to be inserted into the treatment tool guide groove 328 are respectively provided at a distal end and a proximal end of the arm part 406. The rear restriction end 408 and the front restriction end 410 are respectively provided with openings 408A and 410A through which the treatment tool insertion part 202 is inserted. Also, the rear restriction end 408 and the front restriction end 410 restrict the forward and backward movement of the treatment tool coupling part 422 (a treatment tool fixture 450 to be described below), which is disposed inside the treatment tool guide groove 328, in the forward-backward direction therebetween. That is, the rear restriction end 408 and the front restriction end 410 function as a treatment tool locking part of the invention.

A flat first engaging part 404A, which is parallel to an opening of the endoscope guide groove 326 and extends in the forward-backward direction, is formed at the portion of the ring part 404 that faces the endoscope guide groove 326. The rotation of the coupling ring 402 around of the longitudinal axis 300a (hereinafter abbreviated as "around the longitudinal axis") with respect to the partition wall member 324 is restricted by the first engaging part 404A and the aforementioned rear restriction end 408 and front restriction end 410. Additionally, an engaging hole 412 to be described below is formed in the first engaging part 404A.

Also, the coupling ring 402 is supported by the partition wall member 324 so as to be movable forward and backward in the forward-backward direction, and is supported by the partition wall member 324 in a state where the movement of the coupling ring in the upward-downward direction and the rotation of the coupling ring in all directions (direction around three axes including a forward-backward axis, a leftward-rightward axis), and an upward-downward axis are restricted (a state where at least the rotation of the coupling ring around at least the longitudinal axis is impossible). Additionally, the coupling ring 402 moves forward and backward within a movable range having a position, where the rear restriction end 408 of the coupling ring 402 abuts against the proximal end cap 340, as a rear end, and having a position, where the front restriction end 410 of the coupling ring 402 abuts against the distal end cap 360, as a front end.

Figure 7:
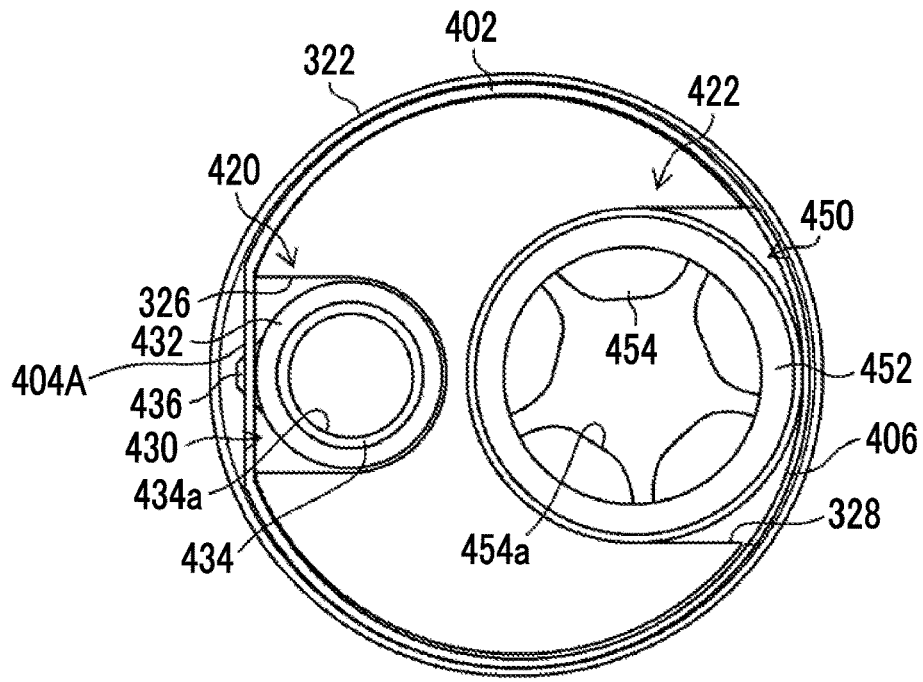
FIG. 7 is a cross sectional view taken along line "7-7" in FIG. 6.
Figure 8A:
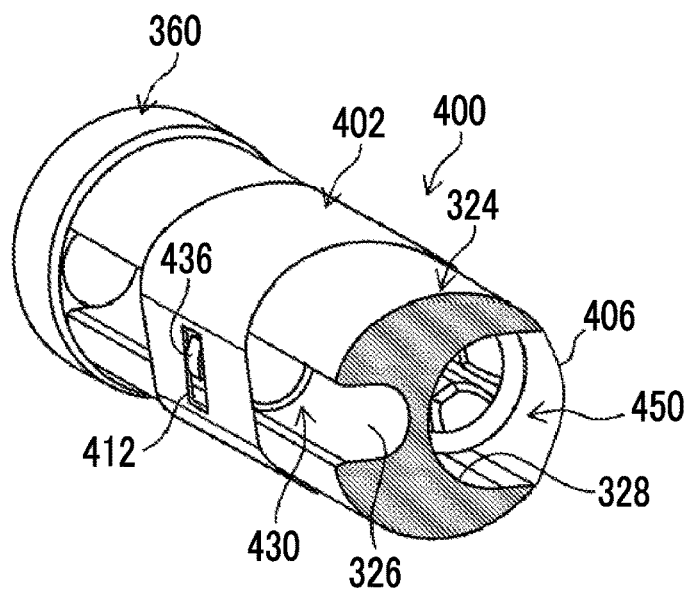
FIG. 8A is a perspective view illustrating the overtube cut in a plane perpendicular to the longitudinal axis at a position intersecting an arm part extending further toward a proximal end side than a ring part in FIG. 3A.
Figure 8B:
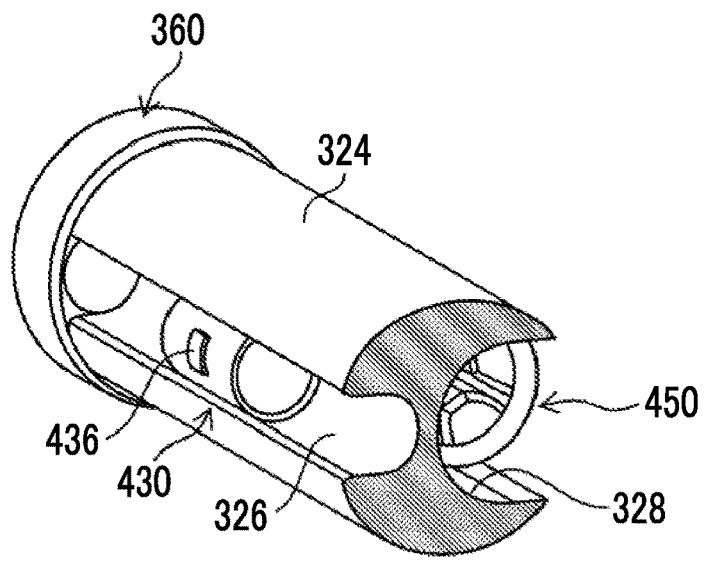
FIG. 8B is a perspective view illustrating FIG. 8A with the coupling ring omitted.
Figure 8C:
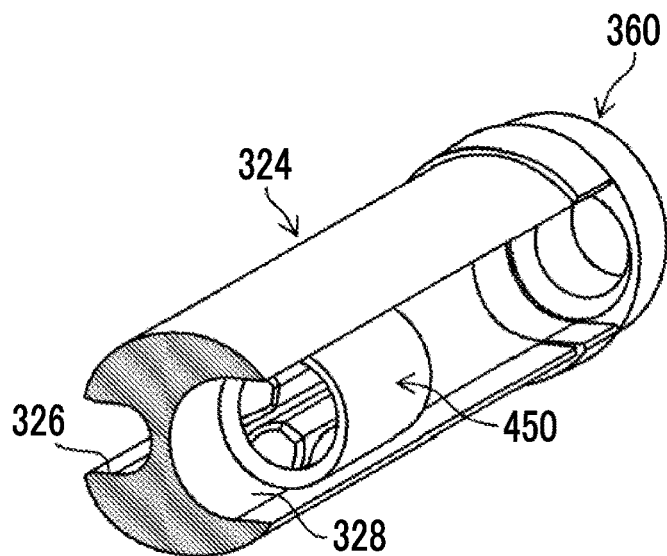
FIG. 8C is a perspective view of the overtube of FIG. 8B as seen from a different direction.

FIG. 7 is a cross sectional view taken along line "7-7" in FIG. 6. FIG. 8A is a perspective view illustrating the overtube 300 cut in a plane perpendicular to the longitudinal axis 300a at a position intersecting the arm part 406 extending further toward the proximal end side than the ring part 404 in FIG. 3A. FIG. 8B is a perspective view illustrating FIG. 8A with the coupling ring 402 omitted. FIG. 8C is a perspective view of the overtube 300 of FIG. 8B as seen from a different direction.

As illustrated in FIGS. 6, 7, and 8A to 8C, the endoscope coupling part 420 is disposed within the endoscope guide groove 326, and is coupled (engaged) with the endoscope insertion part 102 inserted into the endoscope guide groove 326. Additionally, the treatment tool coupling part 422 is disposed within the treatment tool guide groove 328, and is coupled (engaged) with the treatment tool insertion part 202 inserted into the treatment tool guide groove 328.

The endoscope coupling part 420 has an endoscope fixture 430 that is disposed inside the endoscope guide groove 326, and is movable forward and backward in the forward-backward direction along the endoscope insertion passage 306 formed by the endoscope guide groove 326. The endoscope fixture 430 is constituted of a tubular frame 432 that approaches or comes into contact with an inner wall surface of the endoscope guide groove 326, and a tubular endoscope holding part 434, such as an O ring, which is fixed inside the frame 432 and formed of elastic materials, such as elastic rubber.

The frame 432 has a shape such that the movement (rotation) thereof is impossible in the direction around the axis inside the endoscope guide groove 326, and the endoscope fixture 430 is allowed only to move forward and backward in the forward-backward direction within the endoscope guide groove 326.

An outer peripheral part of the frame 432 is provided with a protrusion 436 that protrudes toward the outside of an opening of the endoscope guide groove 326 at a position that faces the opening. The protrusion 436 is inserted through the engaging hole 412, equivalent to an endoscope locking part of the invention, formed in the first engaging part 404A, and is locked in the forward-backward direction. Accordingly, the relative forward and backward movement of the endoscope fixture 430 in the forward-backward direction with respect to the coupling ring 402 is restricted. Therefore, the coupling ring 402 and the endoscope fixture 430 integrally move forward and backward in the forward-backward direction.

The endoscope holding part 434 has an endoscope holding surface 434a (refer to FIG. 7) that is brought into pressure contact (engaged) with an outer peripheral surface of the endoscope insertion part 102 inserted therethrough to hold the endoscope insertion part 102. Accordingly, the endoscope central axis 100a (refer to FIG. 12), which is a central axis of the endoscope 100 (endoscope insertion part 102), is disposed substantially coaxially with the endoscope insertion axis 306a. Since the endoscope holding surface 434a is brought into pressure contact with the outer peripheral surface of the endoscope insertion part 102 due to an elastic force, the endoscope holding surface 434a allows the circumferential rotation of the endoscope 100 about the endoscope central axis 100a. Additionally, the endoscope holding part 434 is able to randomly adjust the holding position of the endoscope insertion part 102 in the forward-backward direction.

Here, such machining processing that a frictional force restricting the rotation of the endoscope insertion part 102 becomes smaller than a frictional force restricting the movement of the endoscope insertion part 102 in the forward-backward direction may be performed on the endoscope holding surface 434a. As this machining processing, for example, a plurality of lateral grooves (refer to the lateral grooves 520 of FIG. 1) are formed in the endoscope holding surface 434a in a circumferential direction thereof. Accordingly, the rotation of the endoscope insertion part 102 can be allowed, and the movement of the endoscope insertion part 102 in the forward-backward direction can be restricted to some extent.

The treatment tool coupling part 422 has the treatment tool fixture 450 that is disposed between the rear restriction end 408 of the aforementioned arm part 406, and the front restriction end 410, inside the treatment tool guide groove 328. The treatment tool fixture 450 is movable forward and backward in the forward-backward direction along the treatment tool guide groove 328 between the rear restriction end 408 and the front restriction end 410.

The treatment tool fixture 450 is constituted of a tubular frame 452 that approaches or comes into contact with an inner wall surface of the treatment tool guide groove 328, and a tubular treatment tool holding part 454, such as O-ring, which is fixed inside the frame 452 and formed of elastic materials, such as elastic rubber. In addition, an inner peripheral surface of the treatment tool holding part 454 is formed in a shape such that regularities are repeated in the circumferential direction so as to be appropriately engageable with even treatment tool insertion parts 202 having a plurality of types of different diameters.

The treatment tool holding part 454 has a treatment tool holding surface 454a that is brought into pressure contact (engaged) with an outer peripheral surface of the treatment tool insertion part 202 inserted therethrough to hold the treatment tool insertion part 202. Accordingly, the central axis of the treatment tool insertion part 202 is disposed substantially coaxially with the treatment tool insertion axis 308a. Since the treatment tool holding surface 454a is brought into pressure contact with the outer peripheral surface of the treatment tool insertion part 202 due to an elastic force, the holding position of the treatment tool insertion part 202 in the forward-backward direction can be randomly adjusted by the treatment tool holding surface 454a.

The treatment tool fixture 450 also integrally moves forward and backward in an interlocking manner with the forward and backward movement of the treatment tool insertion part 202 in the forward-backward direction (axial direction). In this case, the treatment tool fixture 450 is movable forward and backward in the forward-backward direction along the treatment tool guide groove 328 between the rear restriction end 408 and the front restriction end 410, as mentioned above. That is, the arm part 406 allows the forward and backward movement of the treatment tool fixture 450 in the forward-backward direction with respect to the coupling ring 402 in a range from a position where the treatment tool fixture 450 abuts against the rear restriction end 408 to a position where the treatment tool fixture 450 abuts against the front restriction end 410, and restricts the treatment tool fixture 450 in that range.

Additionally, the treatment tool fixture 450 also rotates inside the treatment tool guide groove 328 in an interlocking manner with the rotation of the treatment tool insertion part 202 around the axis thereof.

FIG. 9 is an illustrative view for illustrating a non-sensing region of the coupling ring 402. As illustrated in FIG. 9, in a case where a range where the endoscope fixture 430 is movable forward and backward with respect to the coupling ring 402 is defined as a first range and a range where the treatment tool fixture 450 is movable forward and backward with respect to the coupling ring 402 is defined as a second range, the first range becomes zero because the forward and backward movement of the endoscope fixture 430 in the forward-backward direction with respect to the first engaging part 404A of the coupling ring 402 is restricted as described above. In contrast, the second range is a range between the rear restriction end 408 and the front restriction end 410 as mentioned above. Accordingly, the coupling ring 402 has a non-sensing region where either the treatment tool fixture 450 or the endoscope fixture 430 is not moved forward and backward (interlocked) with the forward and backward movement of the other of the treatment tool fixture 450 and the endoscope fixture 430.

Hence, since the endoscope 100 does not move forward and backward with respect to the forward and backward movement operation of the treatment tool in the non-sensing region (forward and backward movement in a range where the treatment tool fixture 450 and the rear restriction end 408 or the front restriction end 410 do not abut against each other), the range of an observation site, such as a distal end site of the treatment tool 200 and a body cavity inner site, to be displayed on the monitor 112 as an endoscopic image 119 does not vary, and the size of an image of the observation site can be prevented from fluctuating in accordance with minute displacement of the treatment tool 200. Accordingly, a sense of perspective can be suitably maintained, and a stable endoscopic image can be obtained.

Figure 10A:
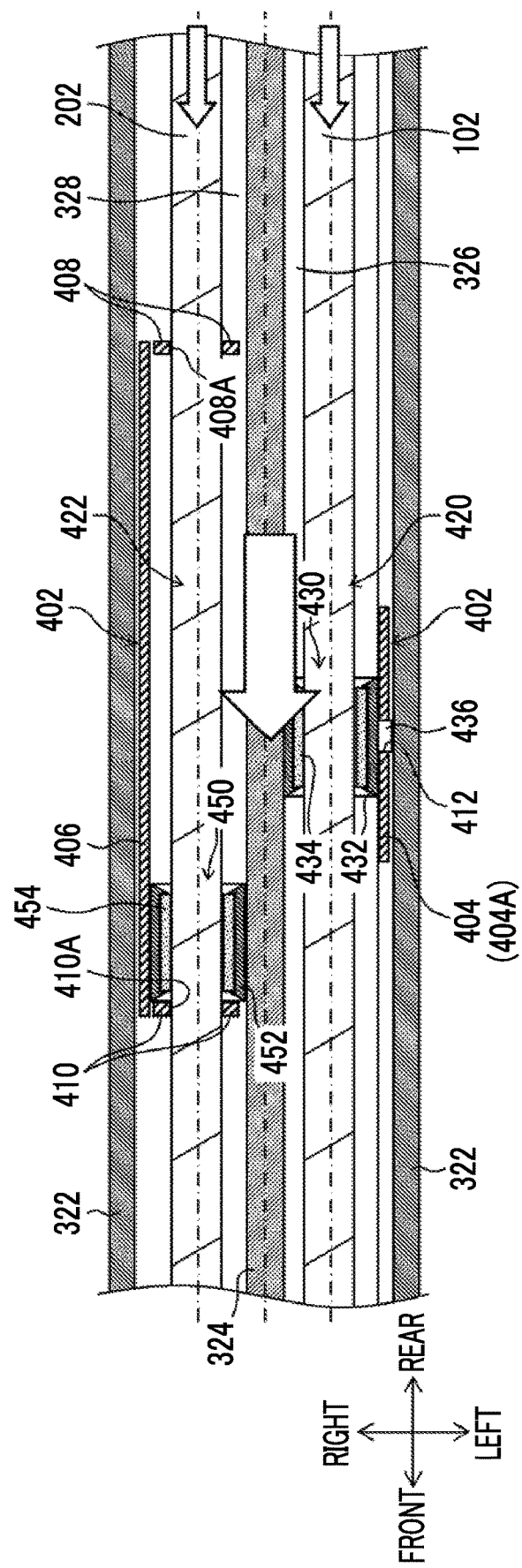
FIG. 10A is an illustrative view for illustrating a sensing region of the coupling ring.
Figure 10B:
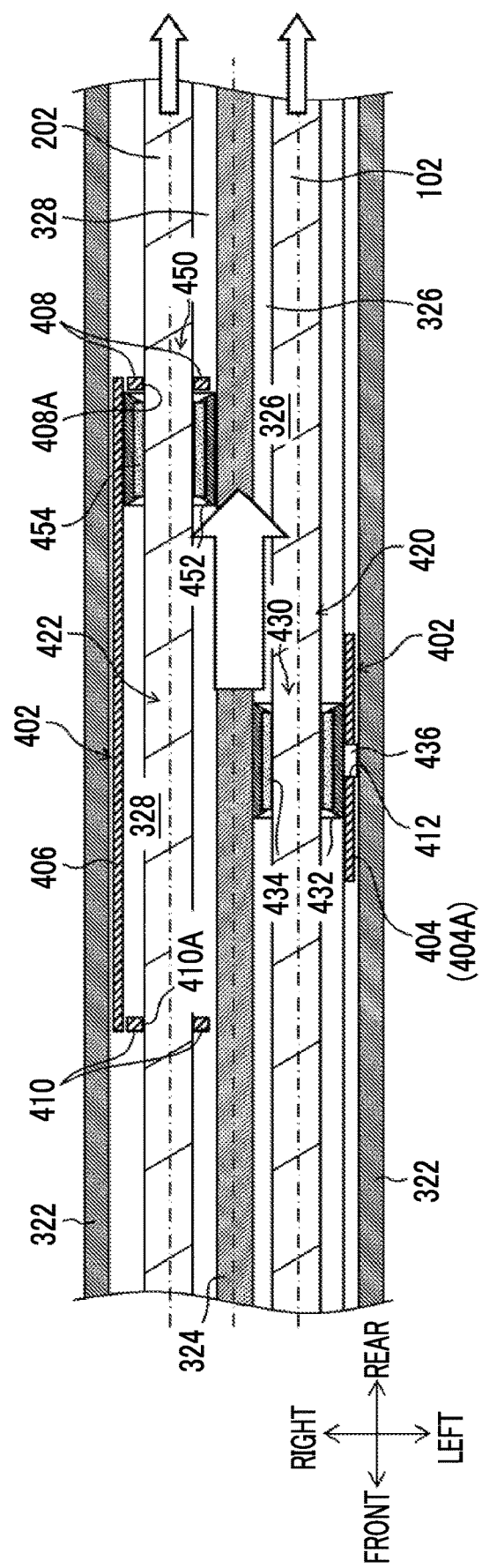
FIG. 10B is an illustrative view for illustrating the sensing region of the coupling ring together with FIG. 10A.

FIGS. 10A and 10B are illustrative views for describing a sensing region of the coupling ring 402. As illustrated in FIGS. 10A and 10B, in a case where the treatment tool fixture 450 has moved forward and backward in the forward-backward direction or in a case where the coupling ring 402 has moved forward and backward in the forward-backward direction together with the endoscope fixture 430, the treatment tool fixture 450 abuts against the rear restriction end 408 or the front restriction end 410. In this state, the coupling ring 402 has a sensing region where either the endoscope fixture 430 or the treatment tool fixture 450 is moved forward and backward movement (interlocked) with respect to the forward and backward movement (the forward and backward movement in a direction in which the treatment tool fixture 450 and the rear restriction end 408 or the front restriction end 410 are not spaced apart from each other) of other of the endoscope fixture 430 and the treatment tool fixture 450.

Since the endoscope 100 moves forward and backward with respect to the forward and backward movement operation in the sensing region, the range of the observation site that appears in an endoscopic image 119 to be displayed on the monitor 112 is continuously changed so as to follow the forward and backward movement of the treatment tool 200. Since the sizes of images of observation sites other than the distal end site of the treatment tool 200 that appears in the endoscopic image 119 in accordance with the operation of the treatment tool 200, and the size of the range of the observation site changes, the operator can simply obtain a desired image.

In this way, the slider 400 has the non-sensing region where the forward and backward movement of either the endoscope insertion part 102 coupled to the endoscope fixture 430 or the treatment tool insertion part 202 coupled to the treatment tool fixture 450 in the forward-backward direction (axial direction) does not interlock with the forward and backward movement of the other and the sensing region where the forward and backward movement of either the endoscope insertion part 102 or the treatment tool insertion part 202 interlocks with the forward and backward movement of the other That is, the endoscope insertion part 102 is adapted to interlock with the forward and backward movement of the treatment tool insertion part 202 in the axial direction with play by the slider 400.

In addition, although the first range where the endoscope fixture 430 is movable forward and backward with respect to the coupling ring 402 is zero in the present embodiment, the forward and backward movement of the endoscope fixture 430 together with the treatment tool fixture 450 with respect to the coupling ring 402 or instead of the treatment tool fixture 450 may be allowed, and the first range may have a magnitude other than zero. Namely, a configuration may be adopted in which the forward and backward movement of at least one of the endoscope fixture 430 and the treatment tool fixture 450 with respect to the coupling ring 402 is allowed.

Additionally, in a case where the forward and backward movement of the endoscope fixture 430 with respect to the coupling ring 402 is allowed, it is possible to adopt a form in which the range, in the forward-backward direction, of the engaging hole 412 of the first engaging part 404A to be engaged with the protrusion 436 of the endoscope fixture 430 is increased. In this case, an end part on a front side of the engaging hole 412 functions as a distal-end-side restricting part of the invention that restricts the movement of the endoscope fixture 430 (endoscope holding part 434) on the distal end side of the slider 400, and an end part on a rear side of the engaging hole 412 functions as a proximal-end-side restricting part of the invention that restricts the movement of the endoscope fixture 430 (endoscope holding part 434) on the proximal end side of the slider 400. Accordingly, the endoscope fixture 430 can be made movable forward and backward with respect to the coupling ring 402 with the length range of the engaging hole 412 in the forward-backward direction as the first range. Moreover, the endoscope fixture 430 can be made movable forward and backward with respect to the coupling ring 402, using the same configuration (equivalent to the distal-end-side restricting part and the proximal-end-side restricting part of the invention) as the rear restriction end 408 and the front restriction end 410 of the arm part 406 with respect to the treatment tool fixture 450.

Additionally, the endoscope fixture 430 may be rotatable around the endoscope insertion axis 306*a* within the endoscope insertion passage 306. In that case, the configuration of the arm part 406 of the coupling ring 402 with respect to the treatment tool fixture 450 can be adopted for the endoscope fixture 430.

In the above embodiment, although the endoscope insertion passage 306 (endoscope insertion axis 306*a*) and the treatment tool insertion passage 308 (treatment tool insertion axis 308*a*) are parallel to the longitudinal axis 300*a*, these axes may not be necessarily parallel to each other.

For example, the treatment tool insertion passage 308 may be disposed parallel to the longitudinal axis 300*a*, and the endoscope insertion passage 306 may be disposed obliquely with respect to the longitudinal axis 300*a*. In this case, since the endoscope fixture 430 moves also in the upward-downward direction with respect to the partition wall member 324 and the coupling ring 402 together with the forward and backward movement thereof in the forward-backward direction, the protrusion 436 formed on the outer peripheral part of the endoscope fixture 430 also moves in the upward-downward direction with respect to the coupling ring 402 in accordance with the position of the endoscope fixture 430 in the forward-backward direction. Thus, the engaging hole 412 is formed as an elongated hole extending in the circumferential direction (upward-downward direction) within the range of the first engaging part 404A or beyond this range.

[Configuration of Endoscope]

Figure 11A:
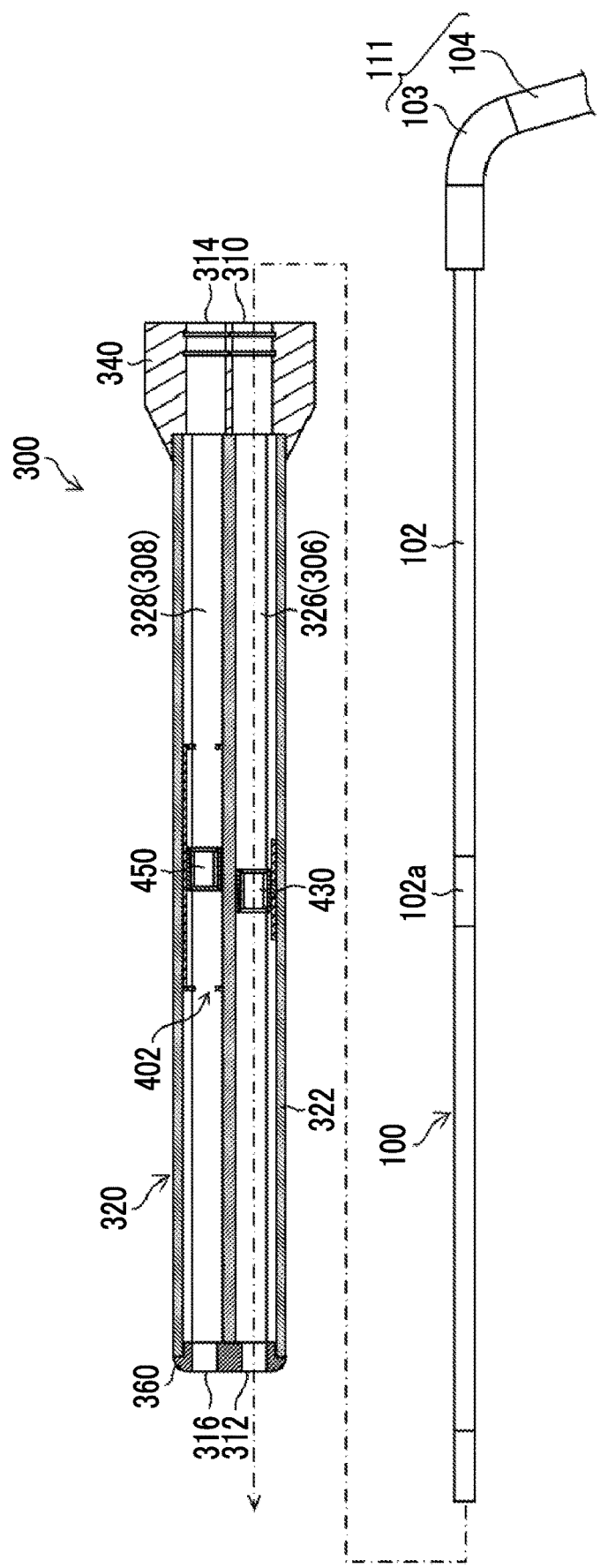
FIG. 11A is a side view of an endoscope before being inserted into the overtube.
Figure 11B:
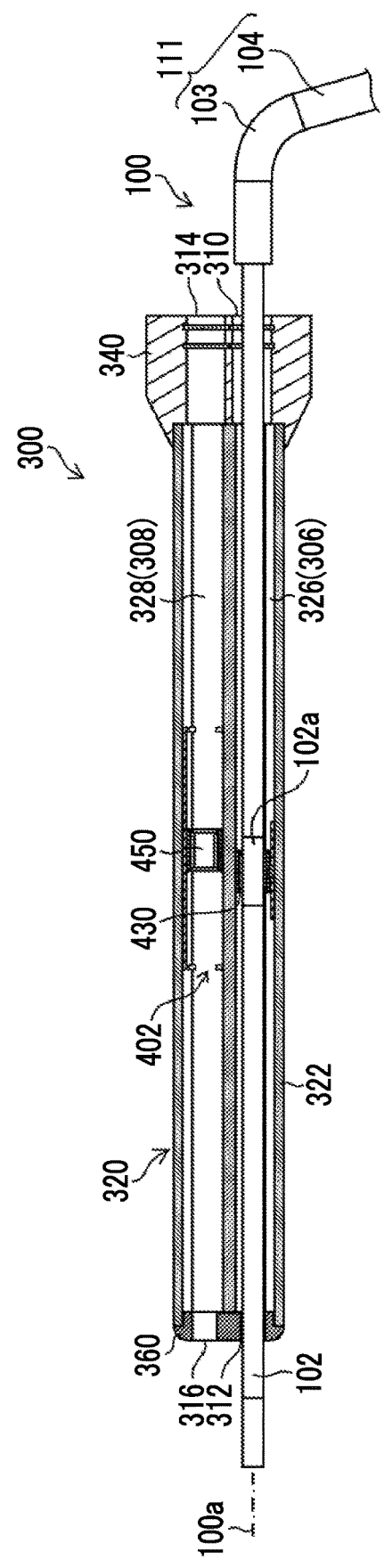
FIG. 11B is a side view of the endoscope after being inserted into the overtube.

FIG. 11A is a side view of the endoscope 100 before being inserted into the overtube 300, and FIG. 11B is a side view of the endoscope 100 after being inserted into the overtube 300. FIG. 12 is an external perspective view of the endoscope 100.

As illustrated in FIGS. 11A, 11B, and 12, the endoscope 100 includes the endoscope insertion part 102, the connecting part 103, and the cord part 104 as already described. The endoscope insertion part 102 is provided with a held surface 102*a* that is held by the endoscope fixture 430 (endoscope holding surface 434*a* of the endoscope holding part 434) so as to be rotatable around the endoscope central axis 100*a* (hereinafter abbreviated as "around the endoscope central axis") in a case where the endoscope insertion part 102 is inserted into the endoscope insertion passage 306 of the overtube 300.

The connecting part 103 and the cord part 104 function as a biasing member 111 of the invention that biases the circumferential position of the endoscope insertion part 102 to a fixed position in a case where the overtube 300 has been rotated around the longitudinal axis with respect to the outer sheath 500.

A portion of the connecting part 103 is provided obliquely with respect to the endoscope central axis 100*a* by being bent with respect to the endoscope insertion part 102. In addition, the bending angle of the connecting part 103 is not particularly limited. The bending direction of the connecting part 103 with respect to the endoscope insertion part 102 (endoscope central axis 100*a*) is a downward direction. As illustrated in FIG. 12, this downward direction is the same (including substantially the same) as a direction b toward a lower-end-side image pick-up region of the solid-state image pick-up element 118 corresponding to a lower end side of the endoscopic image 119 from an upper-end-side image pick-up region of the solid-state image pick-up element 118 corresponding to an upper end side of the endoscopic image 119 displayed on the monitor 112.

Figure 13:
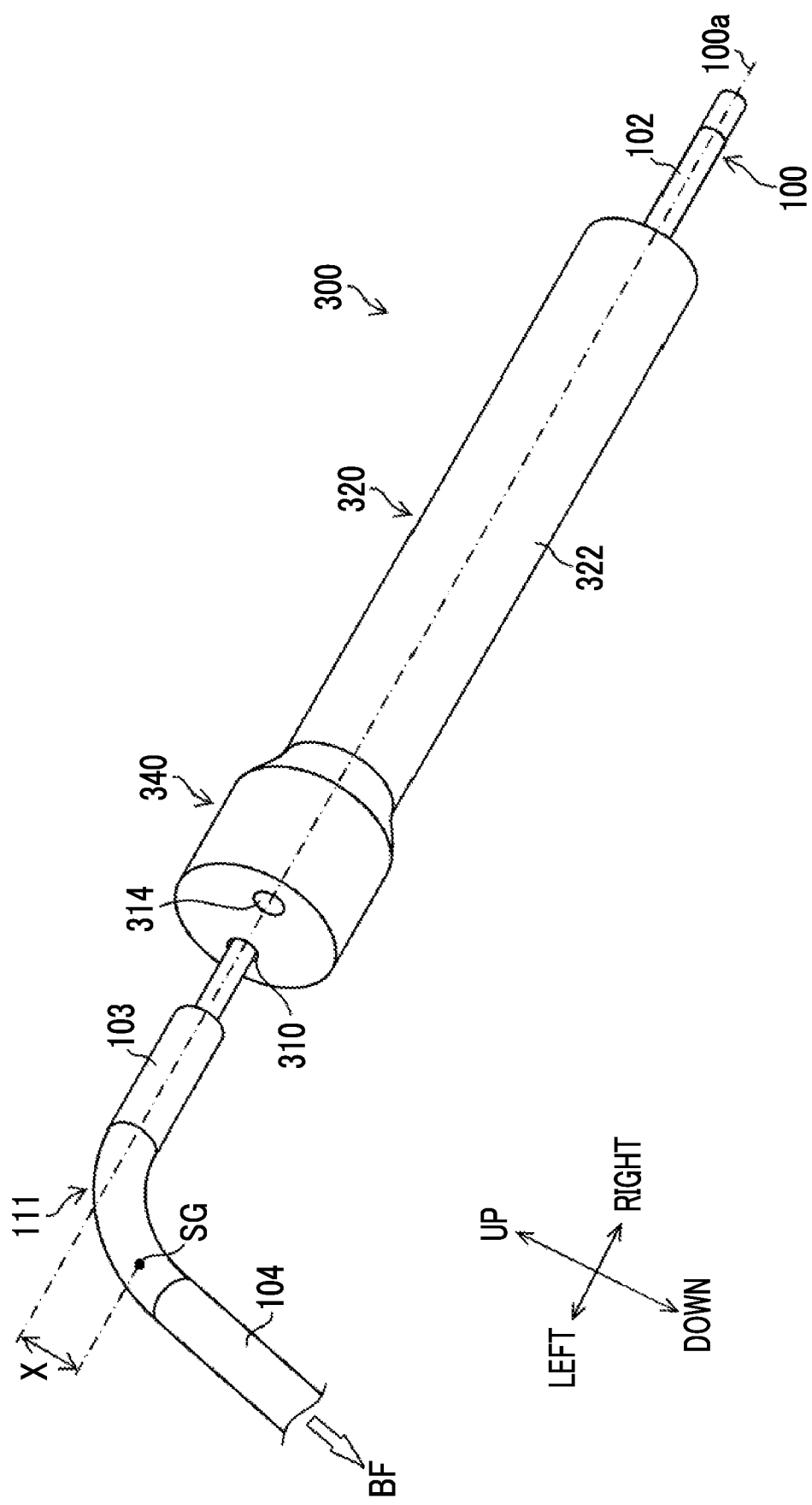
FIG. 13 is an illustrative view for illustrating the gravity center position of a biasing member.

FIG. 13 is an illustrative view for illustrating a gravity center position SG of the biasing member 111 (the connecting part 103 and the cord part 104). As illustrated in FIG. 13, the gravity center position SG of the biasing member 111 including the connecting part 103 and the cord part 104 is a position eccentric (spaced apart) by a predetermined distance X from the endoscope central axis 100*a* of the endoscope insertion part 102 by bending a portion of the connecting part 103. In addition, the gravity center position SG in FIG. 13 is an example, and the position thereof is not particularly limited.

A biasing force BF resulting from the weight of the cord part 104 is added to an end part of the connecting part 103 opposite to a side connected to the endoscope insertion part 102. Here, since the overtube 300, the endoscope 100, and the like are used in a state where these are titled obliquely downward toward a patient side from the operator during the normal treatment of the surgery system 10, the aforementioned gravity center position SG is located below the endoscope central axis 100*a* from an operator's viewpoint. For this reason, the biasing force BF acts on the endoscope insertion part 102 from the connecting part 103 in a direction in which the endoscope insertion part 102 is pushed into the endoscope insertion passage 306, and in a direction in which the endoscope insertion part 102 is rotated such that the orientation of a bending portion of the connecting part 103 bent with respect to the endoscope central axis 100*a* faces downward. As a result, since the endoscope insertion part 102 is held by the endoscope fixture 430 so as to be rotatable around the endoscope central axis, the orientation of the bending portion of the connecting part 103 faces downward.

In addition, in the present embodiment, the frictional force that restricts the movement of the endoscope insertion part 102 in the forward-backward direction by the endoscope fixture 430 as already above is made higher than the frictional force that restricts the rotation of the endoscope insertion part 102. Thus, even in a case where the force has acted on the endoscope insertion part 102 in the direction in which the endoscope insertion part 102 is pushed into the endoscope insertion passage 306, the forward movement of the endoscope insertion part 102 can be restricted. Here, in a case where it is necessary to restrict the forward movement of the endoscope insertion part 102, the forward movement of the endoscope insertion part 102 may be restricted by various techniques, such as providing a restricting part that restricts the forward movement.

In this way, the endoscope insertion part 102 is maintained in an orientation in which the bending portion of the connecting part 103 faces downward by the biasing force BF that acts from the cord part 104 via the connecting part 103. That is, the orientation of the endoscope insertion part 102 around the endoscope central axis is maintained in a fixed direction by the connecting part 103 and the cord part 104.

Figure 14A:
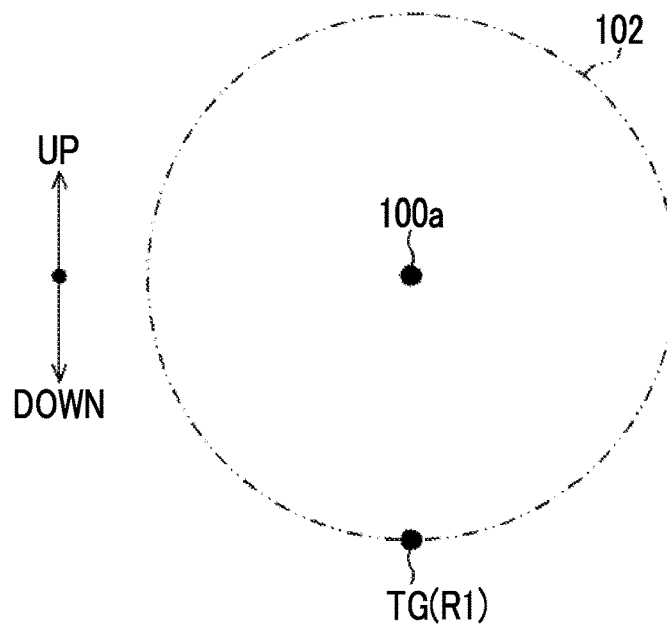
FIG. 14A is an illustrative view for illustrating the maintenance of the orientation of the endoscope insertion part around an endoscope central axis.
Figure 14B:
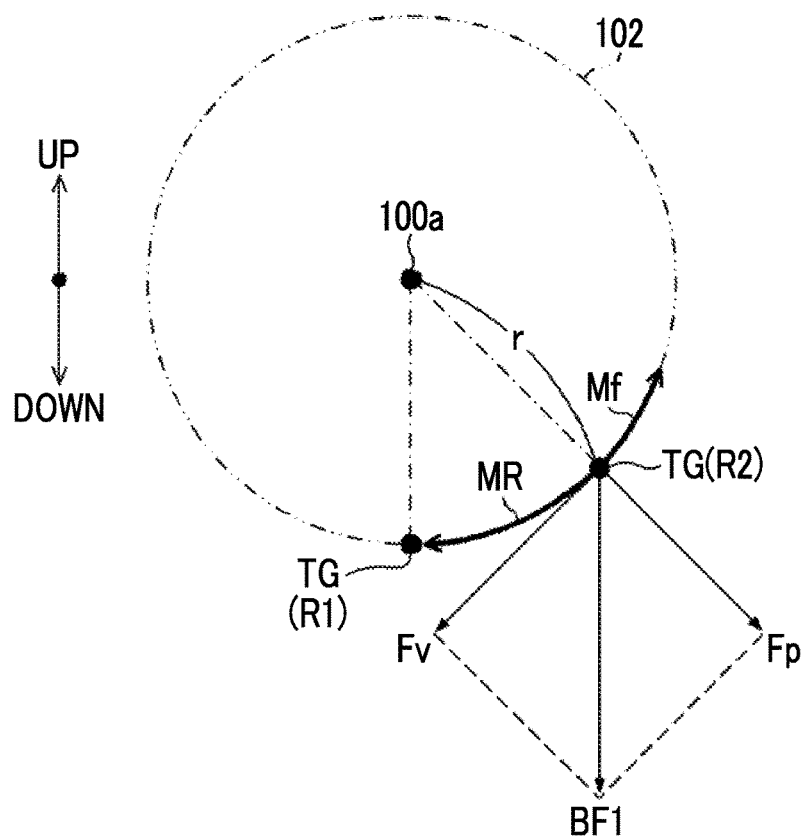
FIG. 14B is an illustrative view for illustrating the maintenance of the orientation of the endoscope insertion part around an endoscope central axis together with FIG. 14A.

FIGS. 14A and 14B are illustrative views for illustrating the maintenance of the orientation of the endoscope insertion part 102 around the endoscope central axis. As illustrated in FIG. 14A, a gravity center position TG in a cross section orthogonal to the endoscope central axis 100*a* of the endoscope insertion part 102 is a position R1 that is eccentric downward from the endoscope central axis 100*a* because the endoscope insertion part 102 receives the action of the biasing force BF from the connecting part 103 and the cord part 104. In addition, the gravity center position TG in the drawing is an example, and any position eccentric downward from the endoscope central axis 100*a* in accordance with the magnitude of the biasing force BF can be taken as the gravity center position.

As illustrated in FIG. 14B, if the endoscope insertion part 102 has rotated around the endoscope central axis and the gravity center position TG has moved from the position R1 to a certain position R2, a rotational moment MR is generated around the endoscope central axis of the endoscope insertion part 102 due to the action of the biasing force BF so as to cancel out this rotation. That is, the connecting part 103 and the cord part 104 (biasing member 111) function as a rotational moment generation part of the invention.

The rotational moment MR is expressed by MR=Fv×r in a case where a downward component of the biasing force BF (refer to FIG. 13) is defined as a biasing force BF1, a component, which is orthogonal to a line segment connecting the endoscope central axis 100*a* and the gravity center position TG, in the biasing force BF1 is defined as Fv, and the distance of the above line segment is defined as r. In addition, although a component Fp parallel to the above line segment in the biasing force BF1 also acts on the gravity center position TG, the movement of the endoscope insertion part 102 in a direction parallel to the above line segment is restricted by the endoscope fixture 430 and the like.

The rotational moment MR is a value that fluctuates depending on the position R2. For this reason, in the present embodiment, the magnitude of the biasing force BF (the length and weight of the cord part 104) and a friction moment Mf is adjusted such that the rotational moment MR become greater than a friction moment Mf about the endoscope central axis 100*a* by a frictional force between the endoscope holding surface 434*a* and the held surface 102*a*, regardless of the position R2.

Therefore, by virtue of the rotational moment MR about the endoscope central axis 100*a* in the gravity center position TG (position R2), the endoscope insertion part 102 rotatably held by the endoscope fixture 430 can be rotated in a reverse direction around the endoscope central axis, and the gravity center position TG can be returned from the position R2 to the position R1. Accordingly, the circumferential position of the endoscope insertion part 102 can be biased to the fixed position (a position of which the gravity center position TG coincides with the position R1) using the rotational moment MR. As a result, even in a case where the overtube 300 has rotated around the longitudinal axis, the circumferential orientation of the endoscope insertion part 102, that is, a state where the bending portion of the connecting part 103 faces downward can be maintained using the rotational moment MR. For this reason, the connecting part 103 and the cord part 104 (biasing member 111) function as an orientation maintaining part of the invention.

Here, the expression "biasing the circumferential position of the endoscope insertion part 102 to the fixed position" or "maintaining the circumferential orientation of the endoscope insertion part 102" also includes a case where the position and orientation of the endoscope insertion part 102 are finally maintained before and after the rotation of the overtube 300 even in a case where a change has temporarily occurred in the circumferential position and orientation of the endoscope insertion part 102 due to the rotation of the overtube 300.

In addition, in a case where the rotational moment MR becomes sufficiently greater than the friction moment Mf even at the position R2 slightly eccentric from the position R1, the endoscope insertion part 102 hardly rotates in the circumferential direction even through the overtube 300 rotates around the longitudinal axis, and can always substantially uniformly maintain the circumferential position and orientation of the endoscope insertion part 102.

[Operation of Surgery System]

Next, the operation of the surgery system 10 of the above configuration will be described with reference to FIG. 15. FIG. 15 is an illustrative view for illustrating changes in the circumferential orientation of the endoscope insertion part 102 of the endoscope 100 in a case where the overtube has rotated around the longitudinal axis, and examples of endoscopic images 119 that are respectively displayed on the monitor 112 in the individual circumferential orientations of the endoscope insertion part 102. Here, reference sign 700 of FIG. 15 is an illustrative view for describing the circumferential orientation of the endoscope insertion part 102 before the overtube 300 rotates around the longitudinal axis, and an example of an endoscopic image 119 displayed on the monitor 112 in this circumferential orientation. Reference sign 701 of FIG. 15 is an illustrative view for describing the circumferential orientation of the endoscope insertion part 102 after the overtube 300 has rotated around the longitudinal axis, and an example of an endoscopic image 119 displayed on the monitor 112 in this circumferential orientation. Reference sign 702 of FIG. 15 is an illustrative view for describing a final circumferential orientation of the endoscope insertion part 102, and an example of an endoscopic image 119 displayed on the monitor 112 in this circumferential orientation. In addition, in FIG. 15, the outer sheath 500 is illustrated in a simplified manner in order to prevent complication of the drawing.

As illustrated in the illustrative view 700 of FIG. 15, in a case where the operator rotates the overtube 300 around the longitudinal axis with respect to the outer sheath 500 in order to change the protruding position of the treatment tool 200 on the endoscopic image 119 displayed on the monitor 112, the gravity center position TG of the endoscope insertion part 102 moves from the position R1 to the certain position R2 (refer to FIG. 14B). As a result, as illustrated in the illustrative view 701, the rotational moment MR about the endoscope central axis 100a in the gravity center position TG (position R2) is generated due to the biasing force BF that acts on the endoscope insertion part 102 from the connecting part 103 and the cord part 104.

Since the rotational moment MR becomes greater than the friction moment Mf about the endoscope central axis 100a as already above, as illustrated in the illustrative view 702, the endoscope insertion part 102 is rotated in the reverse direction around the endoscope central axis due to the rotational moment MR. Accordingly, the circumferential position of the endoscope insertion part 102 can be biased to the fixed position where the gravity center position TG coincides with the position R1 (refer to FIG. 14B) before and after the rotation of the overtube 300.

Even in a case where the overtube 300 has been rotated around the longitudinal axis in this way, the circumferential orientation of the endoscope insertion part 102 can be maintained before and after rotation of the overtube 300 such that the bending portion of the connecting part 103 is brought into a downwardly facing state. For this reason, the position and orientation of the solid-state image pick-up element 118 around an optical axis (not illustrated) can be maintained. That is, the position and orientation of the solid-state image pick-up element 118 around the optical axis are maintained due to the rotational moment MR applied from the connecting part 103 and the cord part 104 (biasing member 111). Therefore, the connecting part 103 and the cord part 104 (biasing member 111) function as a rotational moment application part of the invention. As a result, a change in perspective of the endoscopic image 119, which is finally displayed on the monitor 112, before and after the rotation of the overtube 300, can be suppressed, and the top and bottom of the endoscopic image 119 can be aligned with each other in one direction.

In addition, as already described, in a case where the rotational moment MR becomes sufficiently greater than the friction moment Mf even at the position R2 slightly eccentric from the position R1, the state illustrated in the illustrative view 700 is shifted to the state illustrated in the illustrative view 702 without going through the state illustrated in the illustrative view 701. In this case, even in a case where the overtube 300 is rotated around the longitudinal axis, the endoscope insertion part 102 does not rotate substantially. Thus, the top and bottom of the endoscopic image 119 displayed on the monitor 112 do not change.

Effects of Present Embodiment

Figure 16:
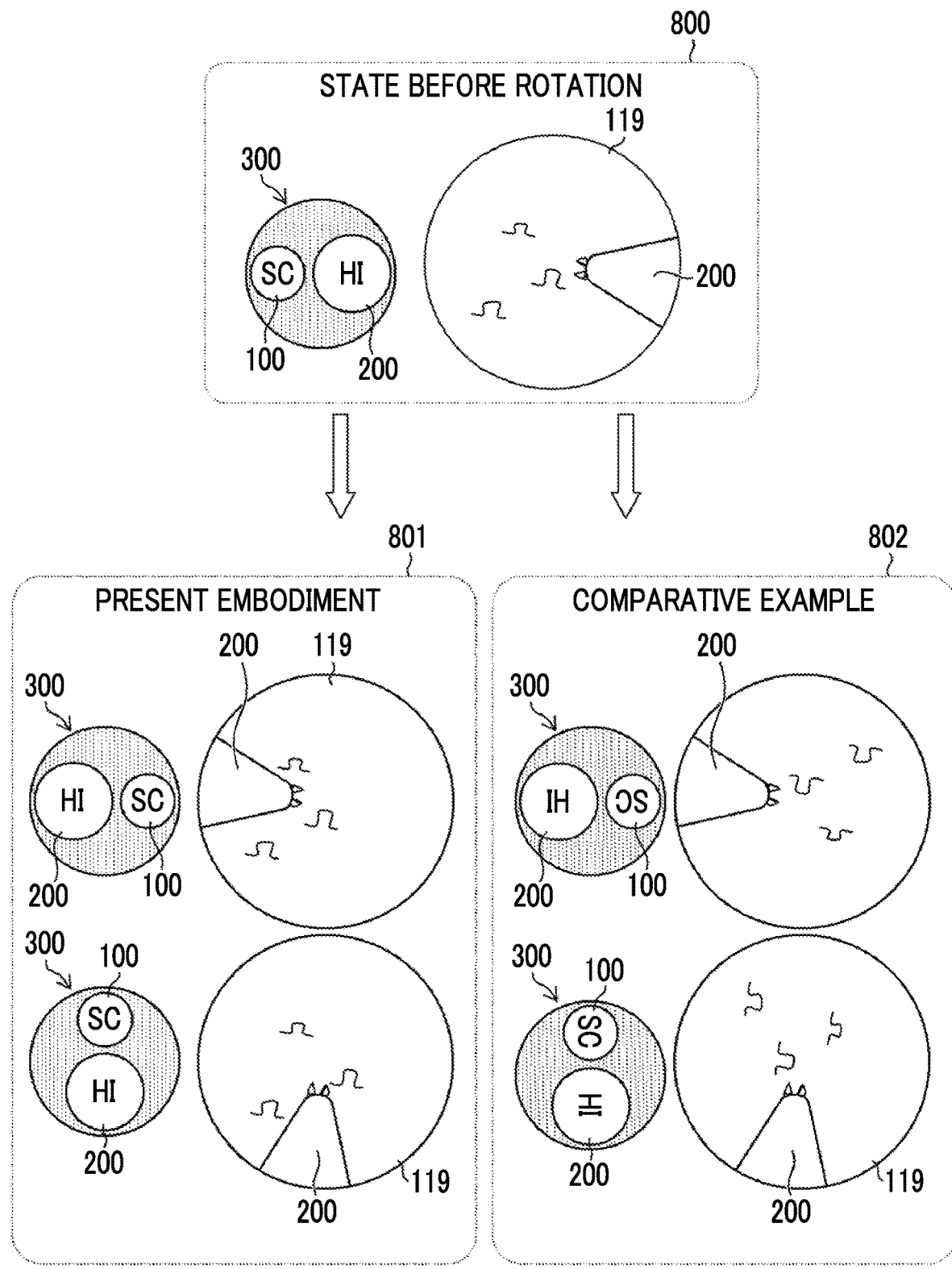
FIG. 16 is an illustrative view for illustrating the effects of the present embodiment and a comparative example, and reference signs 800 to sign 802 illustrate a state before the rotation of the overtube, the effects of the present embodiment, and the comparative example.

FIG. 16 is an illustrative view for illustrating the effects of the present embodiment and a comparative example. Even in a case where the overtube 300 has rotated around the longitudinal axis from the state before the rotation of the overtube 300 as illustrated in an illustrative view 800 in FIG. 16, in the surgery system 10 of the present embodiment as illustrated in an illustrative view 801, the circumferential position and orientation of the endoscope insertion part 102 of the endoscope 100 can be maintained. Thus, a change in perspective of the endoscopic image 119 displayed on the monitor 112 before and after the rotation of the overtube 300 can be suppressed. For this reason, as in a comparative example as illustrated in the illustrative view 802, a situation in which, before and after the rotation of the overtube 300, a situation in which the circumferential position and orientation of the endoscope insertion part 102 change and the top and bottom of the endoscopic image 119 displayed on the monitor 112 change is prevented. As a result, it is possible to make the endoscopic image 119 displayed on the monitor 112 easier to view than the comparative example.

Endoscope of Further Embodiment 1

FIG. 17 is a side view of an endoscope 150 of a further Embodiment 1 that is applicable to the above surgery system 10. The endoscope 100 of the above embodiment maintaining the circumferential position and orientation of the endoscope insertion part 102 using the rotational moment MR generated due to the biasing force BF from the connecting part 103 and the cord part 104 in a case where the overtube 300 has rotated around the longitudinal axis. In contrast, in the endoscope 150, the circumferential position and orientation of the endoscope insertion part 102 are maintained using a weight member 160.

In addition, the endoscope 150 has basically the same configuration as the endoscope 100 of the above embodiment except that the endoscope 150 includes a pillar-shaped connecting part 153 parallel to the endoscope insertion part 102 instead of the connecting part 103 of the above embodiment, and the weight member 160 is provided inside the endoscope insertion part 102 is removed. For this reason, components having the same functions and configurations as those of the above embodiment will be designated by the same reference signs, and the description thereof will be omitted.

As illustrated in FIG. 17, the weight member 160 is equivalent to the biasing member of the invention, and is provided downward of the endoscope central axis 100a inside the endoscope insertion part 102. The weight member 160 adds the biasing force BF, which biases the circumferential position of the endoscope insertion part 102 to the fixed position, to the endoscope insertion part 102 using the weight thereof, thereby maintaining the position and orientation of the endoscope insertion part 102 around the endoscope central axis. In addition, the arrangement and the shape of the weight member 160 are not limited to the arrangement and the shape that are illustrated in FIG. 17, and may be appropriately changed.

Figure 18A:
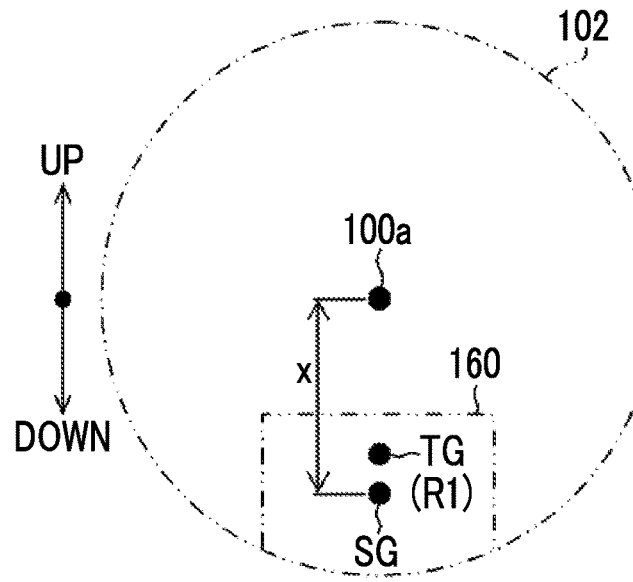
FIG. 18A is an illustrative view for illustrating the gravity center position of an endoscope insertion part of an endoscope of the further Embodiment 1.
Figure 18B:
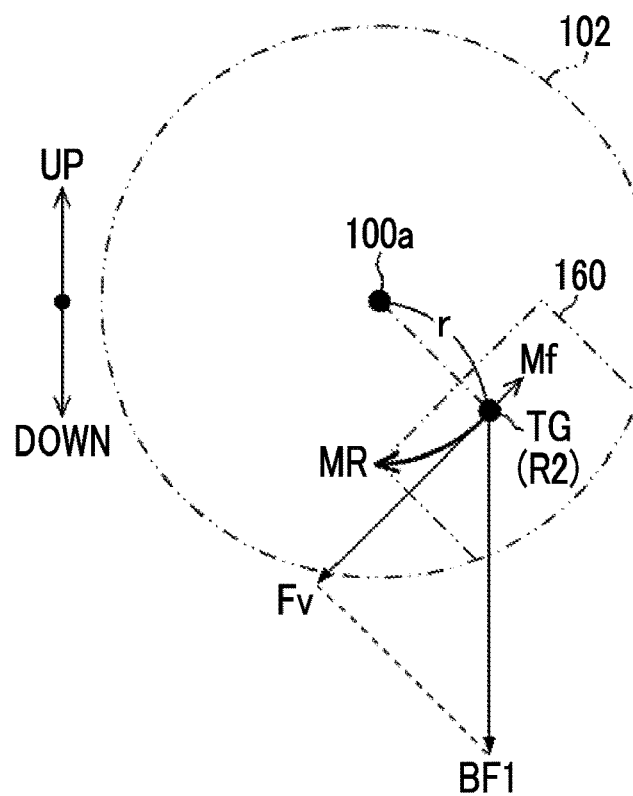
FIG. 18B is an illustrative view for illustrating generation of a rotational moment resulting from a weight member of the endoscope of the further Embodiment 1.
Figure 18C:
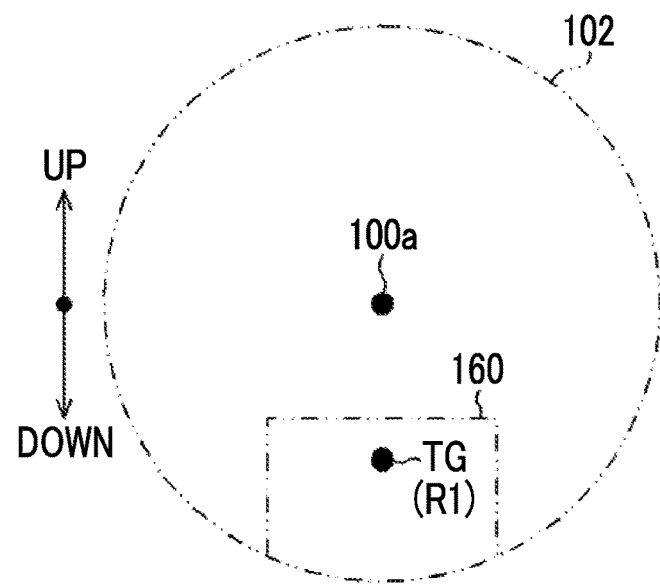
FIG. 18C is an illustrative view for illustrating maintenance of the position and orientation, around the endoscope central axis, of the endoscope insertion part of the endoscope of the further Embodiment 1.

FIG. 18A is an illustrative view for illustrating the gravity center position of the endoscope insertion part 102 of the endoscope 150 of the further Embodiment 1. FIG. 18B is an illustrative view for illustrating the generation of rotational moment MR resulting from the weight member 160 of the endoscope 150 of the further Embodiment 1. FIG. 18C is an illustrative view for illustrating maintenance of the position and orientation, around the endoscope central axis, of the endoscope insertion part 102 of the endoscope 150 of the further Embodiment 1. As illustrated in FIG. 18A, the gravity center position SG of the weight member 160 is a position eccentric by the predetermined distance X downward from the endoscope central axis 100a of the endoscope insertion part 102. For this reason, the gravity center position TG in the cross section orthogonal to the endoscope central axis 100a of the endoscope insertion part 102 is also a position eccentric downward from the endoscope central axis 100a. In addition, the gravity center position SG and the gravity center position TG in the drawing is an example, and any position eccentric downward from the endoscope central axis 100a in accordance with to the shape and weight of the weight member 160, the diameter of the endoscope insertion part 102, or the like can be taken as the gravity center positions.

As illustrated in FIG. 18B, if the endoscope insertion part 102 has rotated around the endoscope central axis and the gravity center position TG has moved from the position R1 downward of the endoscope central axis 100a to a certain position R2, the rotational moment MR is generated around the endoscope central axis of the endoscope insertion part 102 due to the action of the biasing force BF so as to cancel out this rotation, similar to the above embodiment. That is, the weight member 160 functions also as the rotational moment generation part of the invention.

The rotational moment MR is expressed by MR=Fv×r, similar to the above embodiment illustrated in FIG. 14B as already described. In addition, a biasing force BF1 that is a downward component of the biasing force BF becomes equal to the biasing force BF in a case where the endoscope central axis 100a of the endoscope insertion part 102 is kept horizontal. Then, similar to the above embodiment, the weight of the weight member 160 and the magnitude of the friction moment Mf are adjusted such that the rotational moment MR becomes greater than the friction moment Mf regardless of the position R2.

Therefore, by virtue of the rotational moment MR about the endoscope central axis 100a in the gravity center position TG (position R2), the endoscope insertion part 102 can be rotated in the reverse direction around the endoscope central axis as in the above embodiment. Thus, the gravity center position TG can be returned from the position R2 to the position R1 as illustrated in FIG. 18c. Accordingly, the circumferential position of the endoscope insertion part 102 can be biased to the fixed position (a position of which the gravity center position TG coincides with the position R1) using the rotational moment MR. As a result, even in a case where the overtube 300 has rotated around the longitudinal axis, the circumferential orientation of the endoscope insertion part 102 can be maintained in a state where the weight member 160 is located downward of the endoscope central axis 100a. For this reason, the weight member 160 also functions as the orientation maintaining part of the invention. Additionally, since the position and orientation of the solid-state image pick-up element 118 around the optical axis can be maintained using rotational moment MR resulting from the weight member 160, the weight member 160 also functions as the rotational moment application part of the invention.

In addition, for example, in a case where the weight member 160 is sufficiently heavy, the rotational moment MR becomes sufficiently greater than the friction moment Mf regardless of the position R2 as the above embodiment. Thus, even in a case where the overtube 300 has been rotated around the longitudinal axis, the circumferential position and orientation of the endoscope insertion part 102 can always be substantially maintained.

In this way, even in a case where the endoscope 150 of the further Embodiment 1 is applied to the surgery system 10, the circumferential position and orientation of the endoscope insertion part 102 can be maintained in a case where the overtube 300 has been rotated around the longitudinal axis. Thus, the same effects as those of the above embodiment are obtained.

In addition, the weight member 160 may be provided on the outer peripheral surface of the endoscope insertion part 102 within a range where the insertion of the endoscope insertion part 102 into the endoscope insertion passage 306 and the rotation of the endoscope insertion part 102 are not hindered instead of being provided inside the endoscope insertion part 102.

Endoscope of Further Embodiment 2

In the endoscope 150 of the above further Embodiment 1, by disposing the weight member 160 within the endoscope insertion part 102, as illustrated in FIGS. 18A to 18C as already described, the gravity center position TG of the endoscope insertion part 102 is eccentric downward from the endoscope central axis 100a. However, the weight member 160 is not necessary disposed. For example, layout adjustment of various members (the solid-state image pick-up element 118, the observation optical system, and the like) within the endoscope insertion part 102, adjustment of a cross sectional shape of the endoscope insertion part 102, or the like may be performed, and the gravity center position TG may be eccentric downward from the endoscope central axis 100a.

Figure 19:
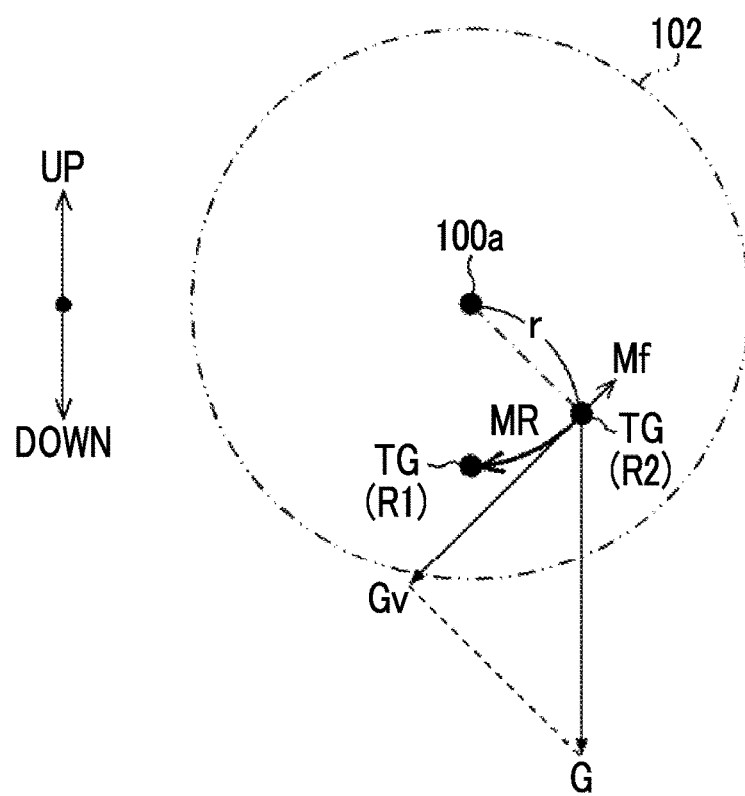
FIG. 19 is an illustrative view for illustrating the generation of a rotational moment resulting from gravity in a still further Embodiment 2.

In this case, as illustrated in FIG. 19, the endoscope insertion part 102 itself functions as the rotational moment generation part, the orientation maintaining part, and the rotational moment application part of the invention, and generates the rotational moment MR, resulting from gravity G, about the endoscope central axis 100a in a case where the overtube 300 has been rotated around the longitudinal axis in the gravity center position TG. In addition, FIG. 19 is an illustrative view for illustrating the generation of the rotational moment MR resulting from gravity G in the further Embodiment 2, and the endoscope central axis 100a will be described herein as being in a horizontal state for simplification of description.

The rotational moment MR is expressed by MR=Gv×r in a case where a component, which is orthogonal to the line segment connecting the endoscope central axis 100a and the gravity center position TG, in gravity G, is defined as Gv, and the distance of the above line segment is defined as r. In addition, in a case where the endoscope central axis 100a is not horizontal, Gv, is a component, orthogonal to the above line segment, in the downward component of gravity G (refer to FIG. 13).

Additionally, in the further Embodiment 2, the gravity center position TG (distance r) and the magnitude of the friction moment Mf are adjusted such that the rotational moment MR becomes greater than the friction moment Mf regardless of the position R2. Accordingly, the endoscope insertion part 102 can be rotated around an endoscope central axis in the reverse direction due to the rotational moment MR, and the gravity center position TG can be returned from the position R2 to the position R1. As a result, similar to the above individual embodiments, even in a case where the overtube 300 has been rotated around the longitudinal axis, the circumferential position of the endoscope insertion part 102 can be biased to the fixed position. As a result, the circumferential orientation of the endoscope insertion part 102 can be maintained.

Others

In the above individual embodiments, the rigid endoscope has been described as an example as the endoscope of the invention. However, the invention can be applied to various kinds of endoscopes to be used by being inserted through the overtube 300.

In the above individual embodiments, the overtube 300 is inserted through the outer sheath 500. However, the invention can also be applied to a case where the overtube 300 directly punctures a body wall without being inserted through the outer sheath 500.

In the above individual embodiments, the gravity center position TG in the cross section orthogonal to the endoscope central axis 100*a* of the endoscope insertion part 102 is eccentric downward from the endoscope central axis 100*a*. However, the gravity center position TG may be eccentric in certain directions other than the downward direction from the endoscope central axis 100*a*.

EXPLANATION OF REFERENCES

- 10: surgery system
- 100: endoscope
- 100*a*: endoscope central axis
- 102: endoscope insertion part
- 102*a*: held surface
- 103: connecting part
- 104: cord part
- 108: processor device
- 110: light source device
- 111: biasing member
- 112: monitor
- 114: distal end surface
- 116: observation window
- 118: solid-state image pick-up element
- 119: endoscopic image
- 150: endoscope
- 153: connecting part
- 160: weight member
- 200: treatment tool
- 202: treatment tool insertion part
- 204: operating part
- 206: treatment part
- 208: sheath
- 210: fixed handle
- 214: movable handle
- 300: overtube
- 300*a*: longitudinal axis
- 302: proximal end surface
- 304: distal end surface
- 306: endoscope insertion passage
- 306*a*: endoscope insertion axis
- 308: treatment tool insertion passage
- 308*a*: treatment tool insertion axis
- 310: first proximal end opening
- 312: first distal end opening
- 314: second proximal end opening
- 316: second distal end opening
- 320: long tubular overtube part
- 322: long tubular body
- 324: partition wall member
- 326: endoscope guide groove
- 328: treatment tool guide groove
- 340: proximal end cap
- 360: distal end cap
- 400: slider
- 402: coupling ring
- 404: ring part
- 404A: first engaging part
- 406: arm part
- 408: rear restriction end
- 408A: opening
- 410: front restriction end
- 410A: opening
- 412: engaging hole
- 420: endoscope coupling part
- 422: treatment tool coupling part
- 430: endoscope fixture
- 432: frame
- 434: endoscope holding part
- 434*a*: endoscope holding surface
- 436: protrusion
- 450: treatment tool fixture
- 452: frame
- 454: treatment tool holding part
- 454*a*: treatment tool holding surface
- 500: outer sheath
- 500*a*: distal end opening
- 500*b*: proximal end opening
- 504: longitudinal groove
- 520: lateral groove
- 700 to 702, 800 to 802: illustrative view
- BF: biasing force
- BF1: biasing force
- G: gravity
- MR: rotational moment
- Mf: friction moment
- SG: gravity center position
- TG: gravity center position
- X: distance
- b: direction
- r: distance

What is claimed is:

1. A surgery system comprising:
an overtube that has a distal end, a proximal end, and a longitudinal axis and holds a treatment tool and an endoscope so as to be movable forward and backward in a direction of the longitudinal axis, the overtube having
an endoscope holding part that has an endoscope holding surface for holding the endoscope and allowing circumferential rotation of the endoscope about a central axis of the endoscope, and
a treatment tool holding part that has a treatment tool holding surface for holding the treatment tool; and
the endoscope that is inserted into the overtube and has a held surface held by the endoscope holding surface, the endoscope having a biasing member that maintains the circumferential orientation of the endoscope even in a case where the overtube rotates around the longitudinal axis, wherein the biasing member has an outer surface,
wherein the biasing member generates a rotational moment around the central axis of the endoscope in a case where the overtube has rotated around the longitudinal axis, and maintains the circumferential orientation of the endoscope using the rotational moment generated in the biasing member,
wherein the overtube has a movable body that is movable in a direction of the longitudinal axis, and the endoscope holding part and the treatment tool holding part are provided at the movable body,
wherein the movable body has a distal-end-side restricting part that restricts movement of the endoscope holding part on a distal end side of the movable body, and a proximal-end-side restricting part that restricts movement of the endoscope holding part on a proximal end side of the movable body, and the endoscope holding part is movable between the distal-end-side restricting part and the proximal-end-side restricting part.

2. The surgery system according to claim 1,
wherein the biasing member biases a circumferential position of the endoscope to a fixed position.

3. The surgery system according to claim 2,
wherein the biasing member has a gravity center position at a position eccentric from the central axis of the endoscope.

4. The surgery system according to claim 2,
wherein the endoscope has a rigid insertion part inserted into the overtube, a flexible cord part provided on a proximal end side of the insertion part, a connecting part connecting the insertion part and the cord part to each other, and at least a portion of the connecting part is provided obliquely with respect to a central axis of the insertion part of the endoscope, and
wherein the biasing member has the connecting part and the cord part, and generates the rotational moment around the central axis of the endoscope with the connecting part and the cord part in a case where the overtube has rotated around the longitudinal axis.

5. The surgery system according to claim 2,
wherein the biasing member is provided inside the endoscope, and biases the circumferential position of the endoscope to a fixed position using a weight of the biasing member.

6. The surgery system according to claim 1,
wherein the endoscope has a gravity center position at a position eccentric from the central axis of the endoscope, and
wherein the biasing member generates the rotational moment, resulting from gravity, about the central axis at the gravity center position of the endoscope.

7. The surgery system according to claim 1,
wherein the movable body has a region where the forward and backward movement of either the endoscope or the treatment tool does not interlock with the forward and backward movement of the other and a region where the forward and backward movement of either the endoscope or the treatment tool interlocks with the forward and backward movement of the other.

8. The surgery system according to claim 1,
wherein the movable body is movable inside the overtube, and
wherein the movable body has an endoscope locking part to which the endoscope holding part is locked, and a treatment tool locking part to which the treatment tool holding part is locked.

9. The surgery system according to claim 1, further comprising:
an outer sheath that has a distal end opening and a proximal end opening and has an insertion passage through which the overtube is inserted from the proximal end opening so as to be rotatable around the longitudinal axis.

10. A surgery system comprising:
an overtube that has a distal end, a proximal end, and a longitudinal axis and holds a treatment tool and an endoscope so as to be movable forward and backward in a direction of the longitudinal axis, the overtube having
an endoscope holding part that has an endoscope holding surface for holding the endoscope, and
a treatment tool holding part that has a treatment tool holding surface for holding the treatment tool; and
the endoscope that is inserted into the overtube and has a held surface held by the endoscope holding surface, the endoscope having a biasing member that generates a rotational moment around a central axis of the endoscope in a case where the overtube has rotated around the longitudinal axis, wherein the biasing member has an outer surface,
wherein the rotational moment generated in the biasing member is greater than a friction moment, about the central axis of the endoscope, resulting from a frictional force between the endoscope holding surface and the held surface,
wherein the overtube has a movable body that is movable in a direction of the longitudinal axis, and the endoscope holding part and the treatment tool holding part are provided at the movable body,
wherein the movable body has a distal-end-side restricting part that restricts movement of the endoscope holding part on a distal end side of the movable body, and a proximal-end-side restricting part that restricts movement of the endoscope holding part on a proximal end side of the movable body, and the endoscope holding part is movable between the distal-end-side restricting part and the proximal-end-side restricting part.

11. The surgery system according to claim 10,
wherein the biasing member biases a circumferential position of the endoscope about the central axis of the endoscope to a fixed position.

12. The surgery system according to claim 10,
wherein the movable body is movable inside the overtube, and
wherein the movable body has an endoscope locking part to which the endoscope holding part is locked, and a treatment tool locking part to which the treatment tool holding part is locked.

13. The surgery system according to claim 12,
wherein the movable body has a region where the forward and backward movement of either the endoscope or the treatment tool does not interlock with the forward and backward movement of the other and a region where the forward and backward movement of either the endoscope or the treatment tool interlocks with the forward and backward movement of the other.

14. A surgery system comprising:
an overtube that has a distal end, a proximal end, and a longitudinal axis and holds a treatment tool and an endoscope so as to be movable forward and backward in a direction of the longitudinal axis, the overtube having
an endoscope holding part that has an endoscope holding surface for holding the endoscope, and
a treatment tool holding part that has a treatment tool holding surface for holding the treatment tool; and
the endoscope that is inserted into the overtube and has a held surface held by the endoscope holding surface, the endoscope having a gravity center position at a position deviating from a central axis of the endoscope,
wherein a rotational moment, resulting from gravity, about the central axis in the gravity center position of the endoscope is greater than a friction moment, about the central axis, resulting from a frictional force between the endoscope holding surface and the held surface,
wherein the overtube has a movable body that is movable in a direction of the longitudinal axis, and the endoscope holding part and the treatment tool holding part are provided at the movable body, wherein the movable body has a distal-end-side restricting part that restricts movement of the endoscope holding part on a distal end side of the movable body, and a proximal-end-side restricting part that restricts movement of the endoscope holding part on a proximal end side of the movable body, and the endoscope holding part is movable between the distal-end-side restricting part and the proximal-end-side restricting part.

15. The surgery system according to claim 14,
wherein the movable body is movable inside the overtube, and
wherein the movable body has an endoscope locking part to which the endoscope holding part is locked, and a treatment tool locking part to which the treatment tool holding part is locked.

16. The surgery system according to claim 15,
wherein the movable body has a region where the forward and backward movement of either the endoscope or the treatment tool does not interlock with the forward and backward movement of the other and a region where the forward and backward movement of either the endoscope or the treatment tool interlocks with the forward and backward movement of the other.

17. The surgery system according to claim 14, further comprising:
an outer sheath that has a distal end opening and a proximal end opening and has an insertion passage through which the overtube is inserted from the proximal end opening so as to be rotatable around the longitudinal axis.

18. A surgery system comprising:
an overtube that has a distal end, a proximal end, and a longitudinal axis and holds a treatment tool and an endoscope so as to be movable forward and backward in a direction of the longitudinal axis, the overtube having
an endoscope holding part that has an endoscope holding surface for holding the endoscope and allowing circumferential rotation of the endoscope about a central axis of the endoscope, and
a treatment tool holding part that has a treatment tool holding surface for holding the treatment tool; and
the endoscope that is inserted into the overtube, the endoscope having an insertion part that has a distal end, a proximal end, and a central axis in a direction of the longitudinal axis, a cord part provided on a proximal end side of the insertion part, a connecting part that connects the insertion part and the cord part to each other, an image pick-up element provided on a distal end side of the insertion part, a held surface provided at the insertion part and held by the endoscope holding surface, a biasing member that applies a rotational moment around the central axis of the insertion part to the image pick-up element, wherein the biasing member has an outer surface and is disposed inside the insertion part,
wherein a center of gravity of the biasing member is at a position eccentric from the central axis of the insertion part,
wherein the overtube has a movable body that is movable in a direction of the longitudinal axis, and the endoscope holding part and the treatment tool holding part are provided at the movable body,
wherein the movable body has a distal-end-side restricting part that restricts movement of the endoscope holding part on a distal end side of the movable body, and a proximal-end-side restricting part that restricts movement of the endoscope holding part on a proximal end side of the movable body, and the endoscope holding part is movable between the distal-end-side restricting part and the proximal-end-side restricting part.

* * * * *